(12) United States Patent  
Doyle et al.

(10) Patent No.: US 8,398,619 B2
(45) Date of Patent: Mar. 19, 2013

(54) FLEXIBLE WRIST-TYPE ELEMENT AND METHODS OF MANUFACTURE AND USE THEREOF

(75) Inventors: Mark Doyle, Del Mar, CA (US); Donald H. Koenig, San Diego, CA (US)

(73) Assignee: Carefusion 2200, Inc., San Diego, CA (US)

( * ) Notice: Subject to any disclaimer, the term of this patent is extended or adjusted under 35 U.S.C. 154(b) by 933 days.

(21) Appl. No.: 12/493,967

(22) Filed: Jun. 29, 2009

(65) Prior Publication Data

US 2009/0320637 A1    Dec. 31, 2009

Related U.S. Application Data

(60) Provisional application No. 61/076,432, filed on Jun. 27, 2008.

(51) Int. Cl.
*A61B 19/00* (2006.01)
(52) U.S. Cl. .............................. 606/1; 606/130
(58) Field of Classification Search ................ 606/1, 130
See application file for complete search history.

(56) References Cited

U.S. PATENT DOCUMENTS

| | | | |
|---|---|---|---|
| 4,848,338 A | 7/1989 | De Satnick et al. |
| 5,456,684 A | 10/1995 | Schmidt et al. |
| 5,496,317 A | 3/1996 | Goble et al. |
| 5,575,799 A | 11/1996 | Bolanos et al. |
| 5,599,350 A | 2/1997 | Schulze et al. |
| 5,611,813 A | 3/1997 | Lichtman |
| 5,618,307 A | 4/1997 | Donlon et al. |
| 5,620,459 A | 4/1997 | Lichtman |
| 5,700,261 A | 12/1997 | Brinkerhoff |
| 5,746,740 A | 5/1998 | Nicholas |
| 5,746,759 A | 5/1998 | Meade et al. |
| 5,752,972 A | 5/1998 | Hoogeboom |
| 5,791,231 A | 8/1998 | Cohn et al. |
| 5,797,941 A | 8/1998 | Schulze et al. |
| 5,820,623 A | 10/1998 | Ng |
| 5,876,410 A | 3/1999 | Petillo |
| 5,931,832 A | 8/1999 | Jensen |
| 6,024,695 A | 2/2000 | Taylor et al. |
| 6,099,536 A | 8/2000 | Petillo |
| 6,102,909 A | 8/2000 | Chen et al. |
| 6,179,837 B1 | 1/2001 | Hooven |
| 6,197,017 B1 | 3/2001 | Brock et al. |
| 6,223,100 B1 | 4/2001 | Green |
| 6,296,635 B1 | 10/2001 | Smith et al. |
| 6,309,397 B1 | 10/2001 | Julian et al. |
| 6,346,072 B1 | 2/2002 | Cooper |
| 6,361,534 B1 | 3/2002 | Chen et al. |
| 6,371,952 B1 | 4/2002 | Madhani et al. |
| 6,391,029 B1 | 5/2002 | Hooven et al. |
| 6,398,726 B1 | 6/2002 | Ramans et al. |
| 6,424,885 B1 | 7/2002 | Niemeyer et al. |
| 6,432,112 B2 | 8/2002 | Brock et al. |
| 6,434,329 B1 | 8/2002 | Dube et al. |
| 6,441,577 B2 | 8/2002 | Blumenkranz et al. |
| 6,468,265 B1 | 10/2002 | Evans et al. |
| 6,488,265 B2 | 12/2002 | Laskaris et al. |
| 6,491,691 B1 | 12/2002 | Morley et al. |
| 6,554,844 B2 | 4/2003 | Lee et al. |
| 6,574,355 B2 | 6/2003 | Green |
| 6,620,174 B2 | 9/2003 | Jensen et al. |
| 6,622,980 B2 | 9/2003 | Boucher et al. |
| 6,665,554 B1 | 12/2003 | Charles et al. |

(Continued)

*Primary Examiner* — Ahmed M Farah
*Assistant Examiner* — Jeffrey Lipitz
(74) *Attorney, Agent, or Firm* — Arent Fox LLP

(57) ABSTRACT

A flexible wrist-type element and methods of operation thereof, including variations having an angularly moveable hub housing a rotatable and operable end effector driven via a drive train having one or more universal-type joints and/or other flexible couplings moveable via an input mechanism within a housing.

29 Claims, 18 Drawing Sheets

U.S. PATENT DOCUMENTS

| | | |
|---|---|---|
| 6,671,581 B2 | 12/2003 | Niemeyer et al. |
| 6,676,669 B2 | 1/2004 | Charles et al. |
| 6,676,684 B1 | 1/2004 | Morley et al. |
| 6,692,485 B1 | 2/2004 | Brock et al. |
| 6,702,805 B1 | 3/2004 | Stuart |
| 6,723,087 B2 | 4/2004 | O'Neill et al. |
| 6,723,106 B1 | 4/2004 | Charles et al. |
| 6,731,988 B1 | 5/2004 | Green |
| 6,746,443 B1 | 6/2004 | Morley et al. |
| 6,755,338 B2 | 6/2004 | Hahnen et al. |
| 6,764,445 B2 | 7/2004 | Ramans et al. |
| 6,770,081 B1 | 8/2004 | Cooper et al. |
| 6,776,783 B1 | 8/2004 | Frantzen et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,788,999 B2 | 9/2004 | Green |
| 6,817,974 B2 | 11/2004 | Cooper et al. |
| 6,827,725 B2 | 12/2004 | Batchelor et al. |
| 6,830,174 B2 | 12/2004 | Hillstead et al. |
| 6,840,938 B1 | 1/2005 | Morley et al. |
| 6,843,793 B2 | 1/2005 | Brock et al. |
| 6,850,817 B1 | 2/2005 | Green |
| 6,860,878 B2 | 3/2005 | Brock |
| 6,866,671 B2 | 3/2005 | Tierney et al. |
| 6,879,880 B2 | 4/2005 | Nowlin et al. |
| 6,936,042 B2 | 8/2005 | Wallace et al. |
| 6,963,792 B1 | 11/2005 | Green |
| 6,991,627 B2 | 1/2006 | Madhani et al. |
| 6,994,708 B2 | 2/2006 | Manzo |
| 6,999,852 B2 | 2/2006 | Green |
| 7,006,895 B2 | 2/2006 | Green |
| 7,048,745 B2 | 5/2006 | Tierney et al. |
| 7,063,697 B2 | 6/2006 | Slater |
| 7,083,615 B2 | 8/2006 | Peterson et al. |
| 7,083,618 B2 | 8/2006 | Couture et al. |
| 7,090,683 B2 | 8/2006 | Brock et al. |
| 7,101,371 B2 | 9/2006 | Dycus et al. |
| 7,107,124 B2 | 9/2006 | Green |
| 7,108,688 B2 | 9/2006 | Jensen |
| 7,125,403 B2 | 10/2006 | Julian et al. |
| 7,155,315 B2 | 12/2006 | Niemeyer et al. |
| 7,155,316 B2 | 12/2006 | Sutherland et al. |
| 7,169,141 B2 | 1/2007 | Brock et al. |
| 7,204,844 B2 | 4/2007 | Jensen et al. |
| 7,246,734 B2 | 7/2007 | Shelton, IV |
| 7,248,944 B2 | 7/2007 | Green |
| 7,250,028 B2 | 7/2007 | Julian et al. |
| 7,252,660 B2 | 8/2007 | Kunz |
| 7,276,065 B2 | 10/2007 | Morley et al. |
| 7,297,142 B2 | 11/2007 | Brock |
| 7,306,597 B2 | 12/2007 | Manzo |
| 7,316,681 B2 | 1/2008 | Madhani et al. |
| 7,320,700 B2 | 1/2008 | Cooper et al. |
| 2002/0120252 A1 | 8/2002 | Brock et al. |
| 2003/0083673 A1 | 5/2003 | Tierney et al. |
| 2003/0109877 A1 | 6/2003 | Morley et al. |
| 2003/0135204 A1 | 7/2003 | Lee et al. |
| 2003/0216715 A1 | 11/2003 | Moll et al. |
| 2003/0236549 A1 | 12/2003 | Bonadio et al. |
| 2004/0039485 A1 | 2/2004 | Niemeyer et al. |
| 2004/0193146 A1 | 9/2004 | Lee et al. |
| 2005/0021018 A1 | 1/2005 | Anderson et al. |
| 2005/0149003 A1 | 7/2005 | Tierney et al. |
| 2005/0215983 A1 | 9/2005 | Brock |
| 2005/0216033 A1 | 9/2005 | Lee et al. |
| 2005/0228440 A1 | 10/2005 | Brock et al. |
| 2005/0240178 A1 | 10/2005 | Morley et al. |
| 2007/0012135 A1 | 1/2007 | Tierney et al. |
| 2007/0021776 A1 | 1/2007 | Jensen et al. |
| 2007/0088340 A1 | 4/2007 | Brock et al. |
| 2007/0093792 A1 | 4/2007 | Julian et al. |
| 2007/0123855 A1 | 5/2007 | Morley et al. |
| 2007/0233052 A1 | 10/2007 | Brock |
| 2008/0033453 A1 | 2/2008 | Brock |

FLEXIBLE WRIST-TYPE ELEMENT AND METHODS OF MANUFACTURE AND USE THEREOF

CLAIM OF PRIORITY

This application for patent claims priority to Provisional Application No. 61/076,432 entitled "FLEXIBLE WRIST-TYPE ELEMENT FOR SURGICAL APPLICATIONS AND METHODS OF MANUFACTURE AND USE THEREOF" filed Jun. 27, 2008, and assigned to the assignee hereof and hereby expressly incorporated by reference herein.

CROSS-REFERENCE TO RELATED APPLICATIONS

This application is related to applicants' co-pending U.S. patent application Ser. No. 11/352,899 titled "HAND-ARTICULATING SURGICAL TOOL" filed Feb. 13, 2006, U.S. patent application Ser. No. 11/775,170 titled "SURGICAL TOOL KIT" filed Jul. 9, 2007, and PCT Appl. No. PCT/US07/86416 titled "INSTRUMENT POSITIONING/HOLDING DEVICES" filed Dec. 4, 2007, the entirety of each of which is hereby incorporated by reference.

BACKGROUND

1. Field of the Invention

Aspects of the present invention relate to a flexible wrist-type element and methods of manufacture and use thereof, including variations having an angularly moveable hub housing and a rotatable and operable end effector driven via a drive train having one or more flexible couplings, such as universal-type joints.

2. Background of the Technology

There is a need for mechanisms for transmitting mechanical force around corners and bends. In one example, these mechanisms are needed in surgical environments to permit work to be performed in difficult-to-reach areas, such as may occur during abdominal surgery. Some mechanisms have been produced in the related art, including push-pull cables in guide tubes, pulley-cable mechanisms, and hydraulic mechanisms, however, none of these related art mechanisms effectively combine such motions as axial and rotary movements so as to allow effective and precise use. For example, flexible push-pull cables have high drag and bending forces; cable-pulley mechanisms are complex and feeble; and hydraulic mechanisms typically are bulky and limited by hose travel.

In another example, there is also a need for mechanisms and features for hydraulically driven mechanisms that, among other things, allow motion and mechanical force transmission around bends to occur without the necessity of delivering hydraulic fluid around such bends, particularly where multiple hydraulic lines may be required (e.g., to produce rotation and grasping operationally downstream of a bend in a hydraulic arm or other extension).

Therefore, improvements in flexible wrist-type elements are desired.

SUMMARY OF THE INVENTION

The described aspects relate to flexible wrist-type elements capable of transmitting axial and/or rotational force around corners and bends. For illustrative purposes, these aspects are discussed herein with respect to a surgical application, however, it should be understood that these aspect may equally apply to many other applications, such as robotics, manufacturing, remote controlled operations, etc., and any application where the transmission of axial and/or rotational force around corners and bends is desired.

Aspects of the present invention include features relating to a flexible wrist-type element for surgical-related activities and methods of manufacture and use thereof, including variations having an angularly moveable hub housing and a rotatable and operable end effector driven via additional drive train elements that include one or more flexible couplings, such as universal-type joints. Force transmitted via the set of such elements includes, for example, lineal force and rotational force.

In one variation, aspects of the present invention include a push-pull-rotate (PPR) element that permits the transmission of axial forces and angular torques around corners or bends. The PPR element may include one or more universal joints (e.g., Hooke's joints) or similarly operating mechanisms arranged in series (in a chain-like configuration) and connected to an input and to an output. The PPR element may be contained within a housing.

In some variations, a guide element is provided to prevent portions of the PPR element from collapsing under compression and to maintain proper form under extension, among other things. Exemplary motion that may be transmitted to the end effector and/or tools via the PPR element may include rotational motion and push-pull or reciprocating motion that may be used, for example, to cause two or more extensions of the end effector to move relative to one another (e.g., to open and close to allow grasping or cutting, and release).

In one variation, the guide element is responsive to the bend angle and is adjusted appropriately or automatically adjusts its position as a function of operation of the device within a motion limiting mechanism, such as a guide track into which an extension from the guide element slides. The bending of the device to various bend angles may be accomplished via use of one or more pivot points and control mechanisms, such as tendon-like linkages. The PPR element may be attached to a source or sources of axial and torsional input (also interchangeably referred to herein as an "input mechanism"), such as a rotatable and extendable and retractable shaft, housed in a body portion. Axial and torsional inputs to each of the PPR elements are then transmitted from the PPR elements to any output, such as to permit rotation and operation of an end effector. The end effector may rotate, for example, relative to the PPR element via a sleeve.

Some variations of the present invention use one or more essentially friction-free or low friction components in the PPR element and guide system, such as rolling-element bearings, which results in relatively high mechanical efficiencies (e.g., as compared to push-pull cables or cable-pulley systems). Other portions of the system relating to movement, such as guide track pins and pivots in some variations, can optionally be replaced with or further include low-friction rolling-element bearings for even smoother action. Appropriate guide track, guide housing, and hub or rotating tip components can comprise non-conductive material to manage the distribution of electrical energy to end-effectors. Any components may be plated with an appropriate anti-friction and/or electrically insulating coating and/or be used with suitable lubricating substance or features.

Conversely or in addition, some portions of the system may be electrically conductive, such as for use in electrosurgery applications. For example the outer housing of the device may be non-conductive, so as to insulate inner conductive portions. The motion transmitting inner portions may be conductive so as to allow electrosurgical current to be delivered to the end effector and/or any tools used therewith, while the outer housing thereby insulates the device. In addition to certain components being conductive, conducting lubricants may also be used to ensure or enhance electrical communication. In some variations, the electrical energy communicated may be of high frequency to enhance communication of the energy across abutting surfaces and lubricants.

In an aspect, a flexible wrist-type element comprises a body housing extending along a first longitudinal axis, a hub and a plurality of couplings. The hub at least partially extends along a second longitudinal axis and is movably connected to the body housing. The hub comprises a first end movable to a first position defining a first angle between the second longitudinal axis and the first longitudinal axis of the body housing, wherein the first angle is variable. The plurality of couplings comprise a plurality of elements movably interconnected by a plurality of joints, wherein the plurality of couplings are movably positionable relative to the body housing and the hub. Further, the plurality of couplings have an input end adjacent to the body housing and an opposing output end adjacent to the first end of the hub, wherein the input end is configured to receive an input force comprising at least one of an axial force or a torsional force. Additionally, the plurality of couplings are configured to transmit at least a portion of the input force from the input end to the output end when the first end of the hub is in the first position defining the first angle.

In another aspect of the flexible wrist-type element described above, the body housing comprises an extension adjacent to the hub, wherein the extension comprises an inner wall defining a surface, wherein the plurality of couplings are in movable contact with the surface, wherein the surface defines limits for movement of the plurality of couplings relative to the body housing and the hub. Optionally, in this aspect, the extension may extend along a third longitudinal axis, and wherein the surface defines a slot having a first length substantially parallel to the third longitudinal axis and a second length substantially perpendicular to the third longitudinal axis, wherein the first length is greater than the second length.

In another aspect, the flexible wrist-type element described above may further comprise a guide element movably connected to the body housing and the hub, wherein the guide element is further movably connected to the plurality of couplings and further comprises a surface, where the surface defines limits for movement of the plurality of couplings. Optionally, in this aspect, the guide element may be movable to a second angle relative to the body housing when the first end of the hub is in the first position defining the first angle relative to the body housing, wherein the second angle is less than the first angle. Optionally, the guide element may further comprise opposing ends, wherein the first guide end is rotatably connected to a first one of the body housing or the hub adjacent to a first one of the opposing ends, and wherein the guide element is slidably connected to a second one of the body housing or the hub adjacent to a second one of the opposing ends.

In another aspect, the flexible wrist-type element described above may further comprise a guide housing movably connected to the body housing and the hub, wherein the guide housing is further movably connected to at least one of the plurality of couplings and comprises a support surface supporting the at least one of the plurality of couplings during movement of the first end of the hub to the first position defining the first angle. Optionally, in this aspect, the support surface may limit an amount of pivoting between the plurality of couplings. In another option of this aspect, the support surface may prevent portions of the plurality of couplings from collapsing under compression and maintains alignment of the plurality of couplings under extension. In yet another option, the body housing may comprise an extension adjacent to the hub, wherein the extension comprises an inner wall defining a first slot, wherein the guide housing further comprises a support element, and further comprising a guide element having a first guide end, a second guide end and a second slot, wherein the first guide end is movably connected to the body housing within the first slot, wherein the second guide end is movably connected to the hub, and wherein the support element of the guide housing is movably connected within the second slot of the guide element such that the second slot defines a limit for movement of the plurality of couplings. Additionally, in another option, the first slot may define an angular limit of the first angle, and wherein the second slot defines an axial limit of movement of the plurality of couplings in response to the input force comprising the axial force. In a further option, the guide housing is connected to the at least one of the plurality of couplings at one of the plurality of joints. In yet another option, the flexible wrist-type element may further comprise a bearing element positioned between the support surface and the at least one of the plurality of couplings, wherein the bearing element allows the at least one of the plurality of couplings to rotate relative to the guide housing.

In another aspect of the flexible wrist-type element described above, each of the plurality of joints comprises a universal joint or a Hooke's joint.

In yet another aspect of the flexible wrist-type element described above, each of the plurality of joints comprises a first pair of ball bearings, spaced apart along a first axis, supporting a first one of the plurality of elements and a second pair of ball bearings, spaced apart along a second axis, supporting a second one of the plurality of elements, wherein the first axis is substantially perpendicular to the second axis.

In still another aspect of the flexible wrist-type element described above, each of the plurality of joints comprises a constant-velocity joint.

In a further aspect of the flexible wrist-type element described above, each of the plurality of elements comprises a first rigid end having a first engagement surface and a second rigid end having a second engagement surface, wherein each of the plurality of joints is defined by a movable interaction between the first engagement surface of a respective first element and the second engagement surface of a respective second element, wherein one of the first engagement surface and the second engagement surface comprises a curved surface. Optionally, in this aspect, each of the plurality of elements further comprises a shaft portion connecting the first rigid end and the second rigid end, further comprising a guide housing having an extending support element and a connection with the shaft that allows relative rotation and prevents relative axial movement, and further comprising a guide element movably connected to the body housing and the hub, wherein the guide element comprises a surface movably connected to the support element of the guide housing, wherein the surface defines limits for movement of the plurality of couplings.

In a further aspect of the flexible wrist-type element described above, the plurality of joints comprise at least three joints.

In yet another aspect, the flexible wrist-type element described above may further comprise a drive system having an input mechanism coupled to the input end of the plurality of couplings, wherein the drive system generates the input force. Optionally, in this aspect, the drive system further generates another force to move the first end of the hub to the first position defining the first angle. In another option of this aspect, the drive system further comprises at least one of an electric system, a hydraulic system, a magnetic system, or a mechanical system.

In yet another aspect, the flexible wrist-type element described above may further comprise a drive system having an input mechanism coupled to the input end of the plurality of couplings, wherein the drive system comprises a manually-driven hydraulic system.

In a further aspect, the flexible wrist-type element described above may further comprise an end effector coupled to the output end of the plurality of couplings, wherein the end effector moves in response to receiving at least the portion of the input force transmitted by the plurality of couplings. Optionally, the end effector comprises a surgical tool.

In yet another aspect, the flexible wrist-type element described above may further comprise a manually-driven hydraulic drive system having an input mechanism coupled to the input end of the plurality of couplings, wherein the drive system generates the input force, and an end effector coupled to the output end of the plurality of couplings, wherein the end effector comprises a surgical tool and moves in response to receiving at least the portion of the input force transmitted by the plurality of couplings.

In yet another aspect of the flexible wrist-type element described above, at least one of the body housing and the hub comprise an electrically non-conductive material, and further comprising an end effector connected to the hub and in communication with an electrically conductive portion within the body housing and the hub, wherein the end effector is configured to receive an electrical current delivered via the electrically conductive portion.

In another aspect, a flexible wrist-type element comprises a body housing extending along a first longitudinal axis, a hub, a plurality of couplings, a guide element, and a guide housing. The hub at least partially extends along a second longitudinal axis and is movably connected to the body housing, wherein the hub comprises a first end movable to a first position defining a first angle between the second longitudinal axis and the first longitudinal axis of the body housing, wherein the first angle is greater than zero degrees. The a plurality of couplings comprise a plurality of elements movably interconnected by a plurality of joints, wherein the plurality of couplings are movably positionable relative to the body housing and the hub. Further, the plurality of couplings have an input end adjacent to the body housing and an opposing output end adjacent to the first end of the hub, wherein the input end is configured to receive an input force comprising at least one of an axial force or a torsional force. Additionally, the plurality of couplings are configured to transmit at least a portion of the input force from the input end to the output end when the first end of the hub is in the first position defining the first angle. Also, the guide element is movably connected to the body housing, the hub and the plurality of couplings, wherein the guide element further comprises a surface that defines limits for movement of the plurality of couplings. The guide element is movable to a second angle relative to the body housing when the first end of the hub is in the first position defining the first angle relative to the body housing, wherein the second angle is less than the first angle. Additionally, the guide housing is connected to the body housing and the hub via a movable connection with the guide element, wherein the guide housing is further movably connected to at least one of the plurality of couplings and comprises a support surface supporting the at least one of the plurality of couplings during movement of the first end of the hub to the first position defining the first angle. Optionally, in this aspect, the flexible wrist-type element may further comprise a manually-driven hydraulic drive system having an input mechanism coupled to the input end of the plurality of couplings, wherein the drive system generates the input force, and an end effector coupled to the output end of the plurality of couplings, wherein the end effector comprises a surgical tool and moves in response to receiving at least the portion of the input force transmitted by the plurality of couplings.

In another aspect, a flexible wrist-type element comprises a body housing extending along a first longitudinal axis, a hub, a plurality of couplings, a guide element, a guide housing, a drive system, and an end effector. The hub at least partially extends along a second longitudinal axis and is movably connected to the body housing, wherein the hub comprises a first end movable to a first position defining a first angle between the second longitudinal axis and the first longitudinal axis of the body housing, wherein the first angle is greater than zero degrees. The plurality of couplings comprise a plurality of elements movably interconnected by a plurality of joints, wherein the plurality of couplings are movably positionable relative to the body housing and the hub. Also, the plurality of couplings have an input end adjacent to the body housing and an opposing output end adjacent to the first end of the hub, wherein the input end is configured to receive an input force comprising at least one of an axial force or a torsional force, and wherein the plurality of couplings are configured to transmit at least a portion of the input force from the input end to the output end when the first end of the hub is in the first position defining the first angle. The guide element is movably connected to the body housing, the hub and the plurality of couplings, wherein the guide element further comprises a surface that defines limits for movement of the plurality of couplings, wherein the guide element is movable to a second angle relative to the body housing when the first end of the hub is in the first position defining the first angle relative to the body housing, wherein the second angle is less than the first angle. The guide housing is connected to the body housing and the hub via a movable connection with the guide element, and the guide housing is further movably connected to at least one of the plurality of couplings and comprises a support surface supporting the at least one of the plurality of couplings during movement of the first end of the hub to the first position defining the first angle. The drive system has an input mechanism coupled to the input end of the plurality of couplings, wherein the drive system generates the input force. And, the end effector is coupled to the output end of the plurality of couplings, wherein the end effector moves in response to receiving at least the portion of the input force transmitted by the plurality of couplings. Optionally, in this aspect, the drive system comprises a manually-driven hydraulic system, and wherein the end effector comprises a surgical tool.

Additional advantages and novel features relating to the present invention will be set forth in part in the description that follows, and in part will become more apparent to those skilled in the art upon examination of the following or upon learning by practice of aspects of the invention.

BRIEF DESCRIPTION OF THE DRAWINGS

The present invention will become fully understood from the detailed description given herein below and the accompanying drawings, which are given by way of illustration and example only and thus not limitative with respect to aspects of the present invention, wherein.

DETAILED DESCRIPTION

Aspects of the present invention now will be described more fully hereinafter with reference to the accompanying drawings, in which variations and aspects of the present invention are shown. Aspects of the present invention may, however, be realized in many different forms and should not be construed as limited to the variations set forth herein; rather, these variations are provided so that this disclosure will be thorough and complete in the illustrative implementations, and will fully convey the scope thereof to those skilled in the art.

Unless otherwise defined, all technical and scientific terms used herein have the same meaning as commonly understood by one of ordinary skill in the art to which aspects of the present invention belong. The methods and examples provided herein are illustrative only and not intended to be limiting.

By way of introduction, aspects of the present invention include a flexible wrist-type element for use in surgical-related activities and methods of operation thereof, including variations having an angularly moveable hub housing, and a rotatable and operable end effector driven via additional elements in a drive train that may include one or more universal-type joints or other similarly flexible motion transmitting mechanisms.

Figure 1:
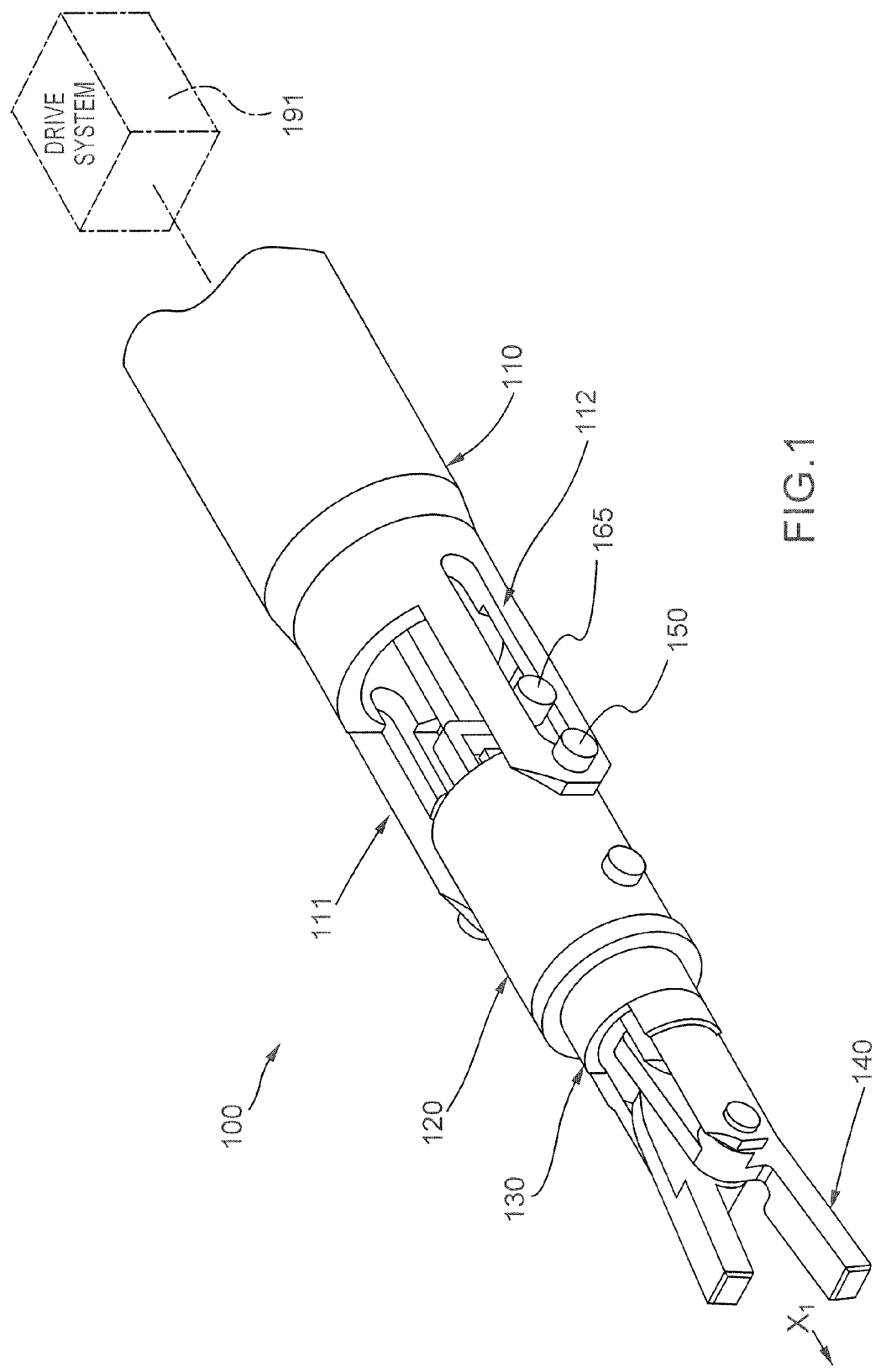
FIG. 1 shows a view of an exemplary flexible wrist-type element, in accordance with aspects of the present invention.

FIG. 1 shows a perspective view of an exemplary flexible wrist-type element 100, in accordance with aspects of the present invention. As shown in FIG. 1, the flexible wrist-type element 100 has a body housing 110 that is coupled to or otherwise operably engages a hub 120. Among other things, the hub may move angularly relative to the housing 110 (compare, e.g., the position shown in FIG. 3) about, for example, one or more pivot points 150. Optionally, an end effector or other tool or component 140 (also interchangeably and/or collectively referred to herein as an "end effector") is engaged with the hub 120, such as via a sleeve 130 that allows relative rotation with respect to the hub 120. In another option, a drive system 191 may be operative coupled to the wrist-type element 100, wherein the 191 system generates forces for moving the hub 120 relative to the body housing 110 and/or for moving the end effector 140, for example, to perform useful work.

In the view of FIG. 1, the body housing 110, hub 120, and end effector 140 are shown positioned in approximately linear alignment along each of these elements' axial lengths in direction $X_1$. Also shown in FIG. 1 is a movement limiting travel mechanism, such as a slot 112 in extension 111 extending from or attached to body housing 110, which limits travel of a slidable guide track pin 165, the operation of which will be described further below.

Figure 2:
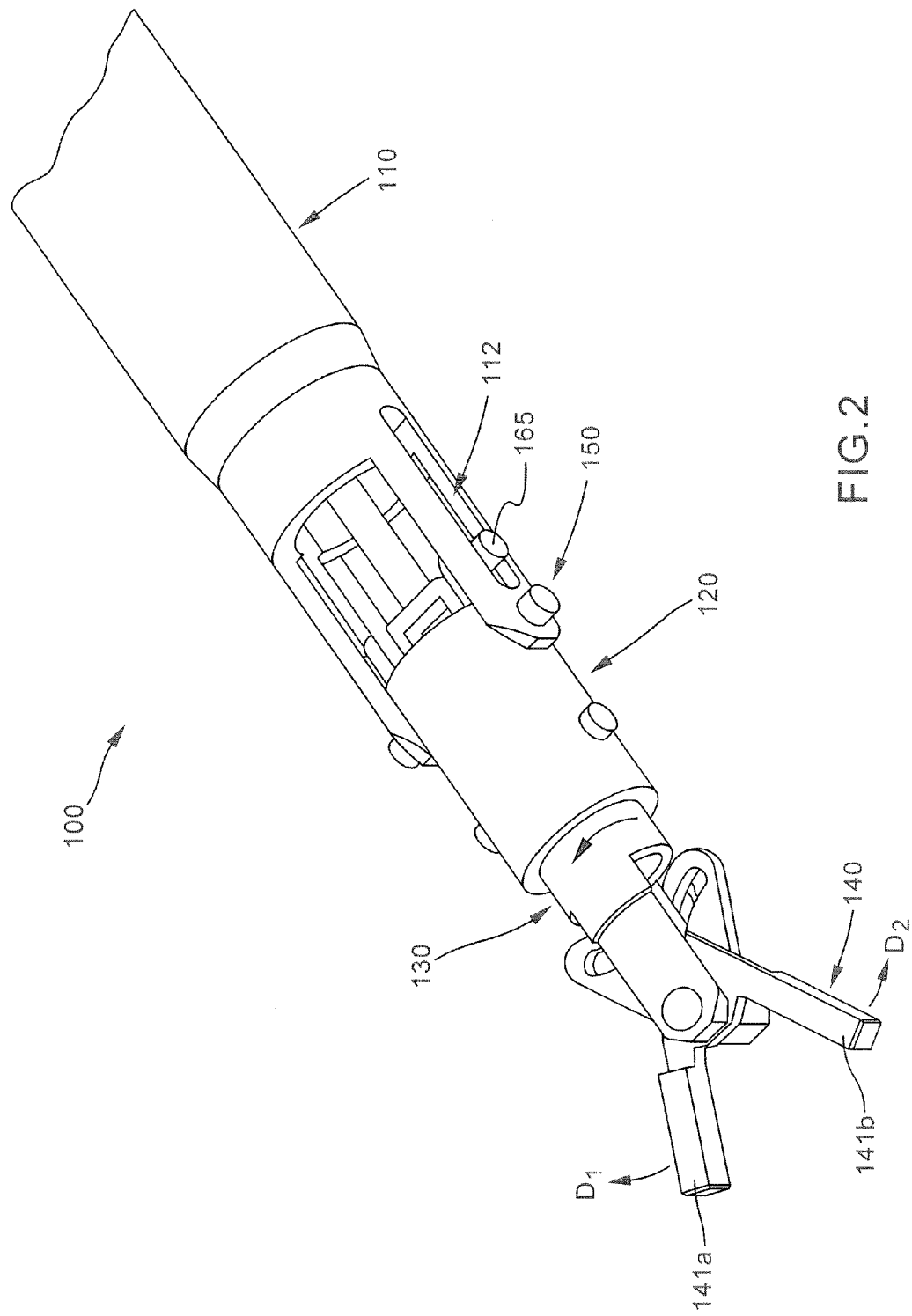
FIG. 2 shows the flexible wrist-type element of FIG. 1, with the end effector portion rotated and in an open position, relative to the position of FIG. 1.

FIG. 2 shows the flexible wrist-type element 100 of FIG. 1, with the end effector portion 140 rotated and in an "open" position (with regard to the two extensions 141a, 141b), relative to the position shown in FIG. 1. As indicated in FIG. 2, the sleeve 130, as shown, is rotatable relative to the hub 120, such as to the position shown. For example, the sleeve 130 may include one or more extensions, a lip, or other similar feature or features extending from its exterior surface for engagement with a receiving opening or other corresponding feature in the hub 120. Other methods and/or features may similarly be used to enable such relative rotational motion. In addition, as shown in FIG. 2, end effector portion 140 may be manipulated, such as by moving arms or extensions 141a, 141b relative to each other (e.g., opening in directions $D_1$, $D_2$). Further details of operation and control of sleeve 130 and end effector portion 140 will be described further below.

Figure 3:
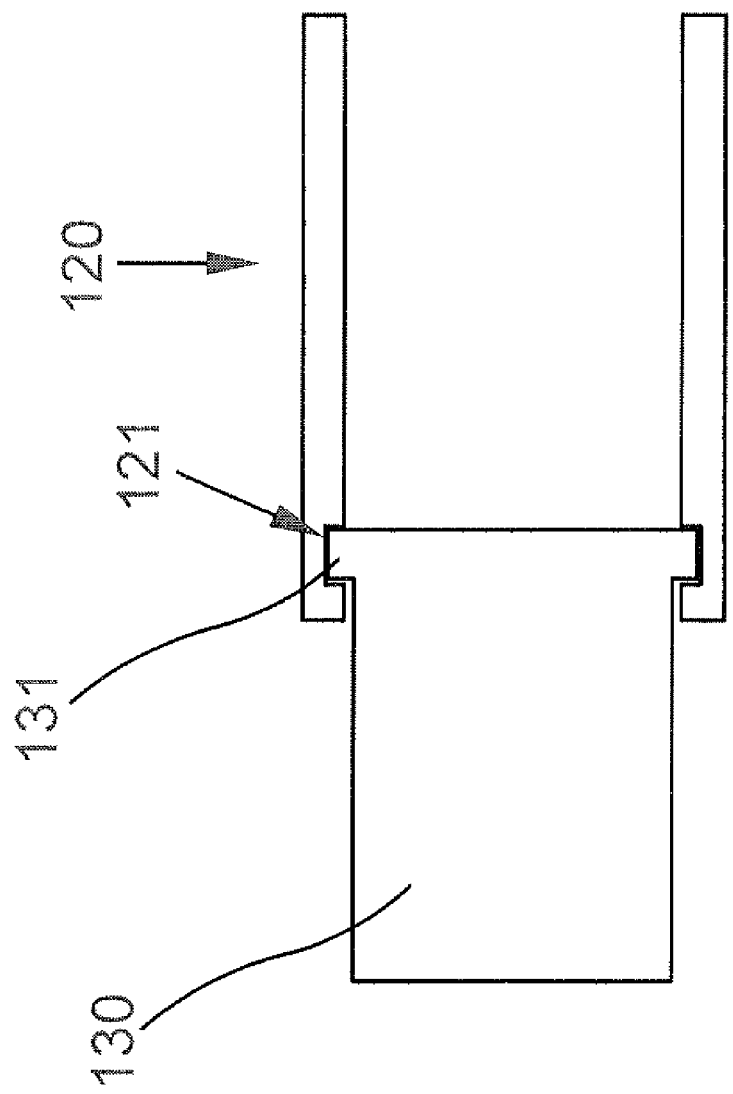
FIG. 3 shows a partial cutaway view of various elements of an exemplary hub and end effector sleeve enabling relative rotation therebetween, in accordance with aspects of the present invention.

FIG. 3 shows a representative partial cutaway view of a portion of an exemplary sleeve 130 and hub 120 engageable in accordance with one exemplary variation of features so as to allow relative rotation therebetween. As shown in FIG. 3, the sleeve 130 has an extending lip 131 about its outer circumferential surface that is engageable within a groove 121 in the interior surface of the hub 120, thereby allowing sliding rotation of the sleeve 130 relative to the hub 120.

Figure 4:
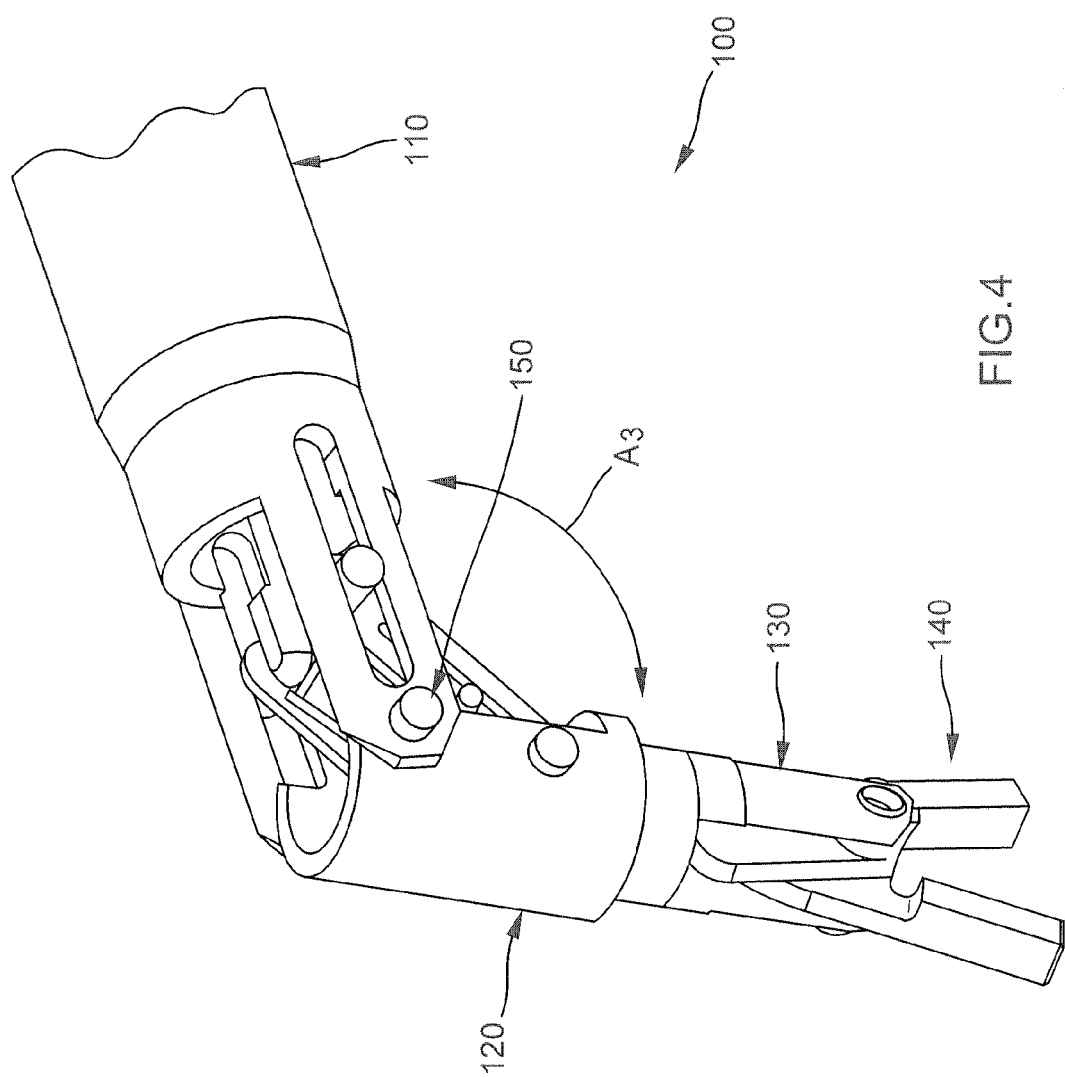
FIG. 4 shows the flexible wrist-type element of FIG. 1 oriented such that the hub portion is angled relative to the body portion.

FIG. 4 shows an exemplary flexible wrist-type element 100 in accordance with aspects of the present invention similar to the device shown in FIG. 1, that is oriented to a position such that the hub portion 120 is moved angularly to an angle $A_3$ relative to the body housing 110. Such angular operation may occur via a control rod or other tendon-like element, for example, not visible in FIG. 4. For example, the control rod or other tendon-like element may be a mechanism to transmit force, such as a link connected between the hub portion 120 and a bend actuator (not shown). Operation and control of the element 100 will be described further below.

Figure 5:
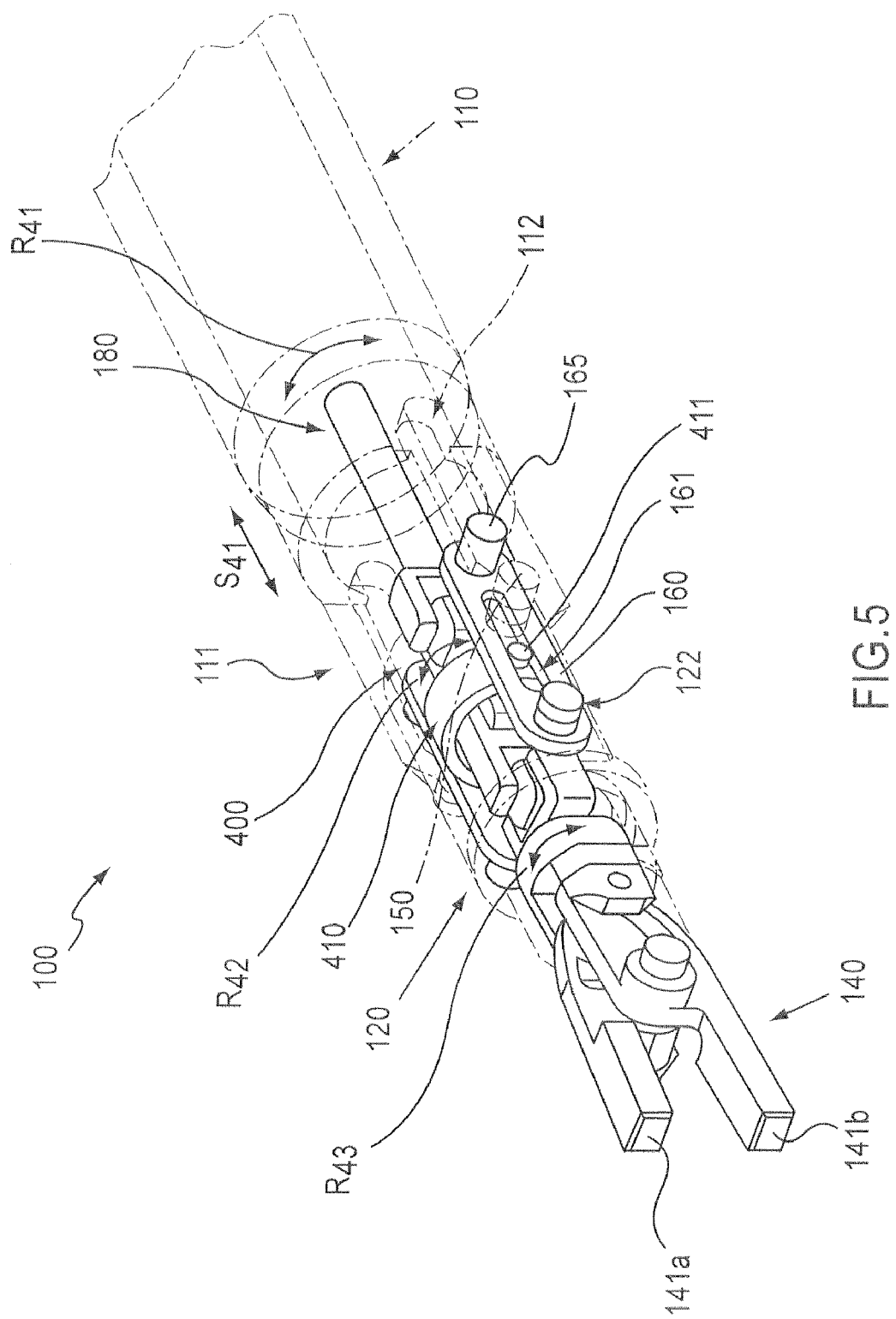
FIG. 5 presents a partial cutaway view of one exemplary flexible wrist-type element, in accordance with aspects of the present invention, in a similar position to that shown in FIG. 1.

FIG. 5 presents a partial cutaway view of an exemplary flexible wrist-type element 100 in a similar position to that shown in FIG. 1. As shown in FIG. 5, extending from the interior of housing body 110 is an input mechanism (e.g., shaft) 180. Coupled to or otherwise operable via the input mechanism 180 are one or more flexible couplings 400, such as universal joints and/or Hooke's joints. It should be noted that increasing the number of couplings 400 may increase the mechanical efficiency of the transmission of the axial forces through the couplings 400 when the hub portion 120 and/or end effector 140 is angled relative to the body housing 110, as each additional coupling 400 reduces a relative joint angle between adjacent couplings, thereby improving axial force transmission. Optionally, in some aspects, one or more guide housings 410 may be may be movably connected to one or more of the flexible couplings 400 for securing and/or limiting the travel of one or more of the flexible couplings. In the variation shown, at least one guide housing 410 has or is attached to a travel limiting movement mechanism, such as pin 411 slidable within a guide 160. In the exemplary variation shown in FIG. 5, three flexible couplings 400 are coupled in series to the input mechanism 180, and the guide 160 is secured at one end via a first pin 165 slidable within slot 112 and at a second end via a second pin 122 secured to the hub 120.

In exemplary operation, for example, as shown in FIG. 5, input mechanism 180 comprises an input shaft coupled to the flexible coupling(s) 400, which in this aspect includes three universal joints coupled in series, the flexible coupling(s) 400 being further coupled to the end effector 140 via an end effector shaft (one or more of the input mechanism 180, the flexible couplings 400, and/or parts of the end effector 140 interchangeably also being referred to herein as a "drive train"). The guide 160 is secured and/or limited in movement at its two ends by a first pin 165 that travels within the slot 112 of extension 111 and by a second pin 122 attached to the hub 120. The guide housing 410 is coupled to the middle of the three universal joints in series. The guide housing 410 includes an extending pin 411 that is limited in its travel by slot 161 of guide 160. It is noted that, in the position shown in FIG. 5, the first pin 165 is located near a first end of the slot 112.

The input shaft of the input mechanism 180 may be moved (e.g., by sliding) with the flexible coupling(s) 400 (e.g., in direction $S_{41}$ as shown in FIG. 5). As noted above, drive system 191 may be coupled to the input mechanism 180 causing the input mechanism 180 to move. Drive system 191 provides, at least one of axial force or torsional force to the couplings 440. For example, the drive system 191 may include one or any combination of a hydraulic system, a magnetic system, a mechanical system, or an electrical system (e.g., servo motors), among other systems. Further, in one aspect, which should not be construed as limiting, the drive system 191 comprises a manually-driven hydraulic system, such as a system operated by manual movements of a person, such as a surgeon, who move hydraulic fluid through tubes to generate the force or motion at input mechanism 180. The force or motion of input mechanism 180 in turn produces motion (e.g., in direction $S_{41}$ in the orientation of the device 100 shown in FIG. 5) of the flexible couplings, which may travel together with the guide housing 410 within the limits of slot 161. Among other things, the guide housing 410 ensures that the three universal joints do not pivot significantly relative to one another in a direction other than the direction of travel (i.e., generally in direction $S_{41}$ as shown in FIG. 5). The motion in direction $S_{41}$ of the universal joints may in turn affect the end effector 140, such as by causing the extensions 141a, 141b to open and close.

The input shaft as shown in FIG. 5 may also be rotated, for example, in directions $R_{41}$, which in turn rotates the universal joints in corresponding directions $R_{42}$ and rotates the end effector in corresponding directions $R_{43}$.

Figure 6:
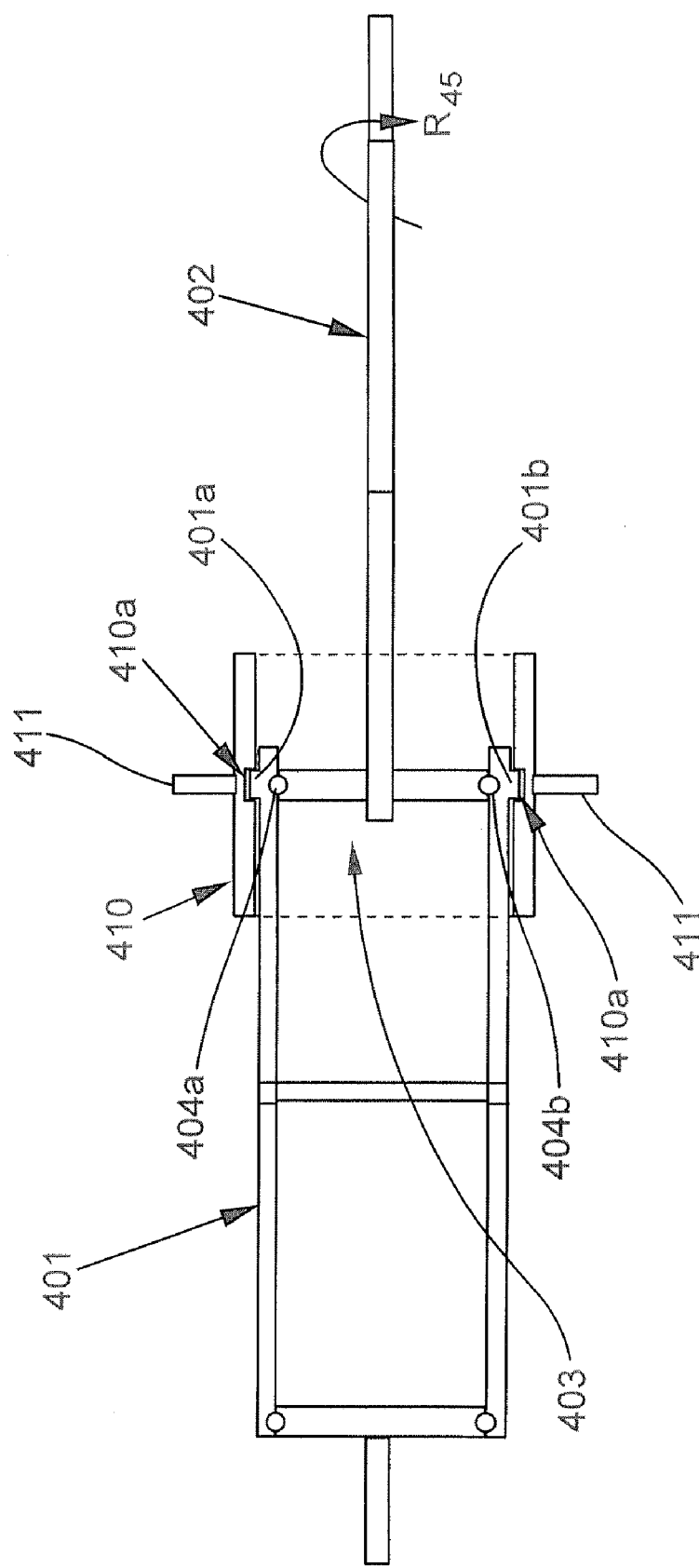
FIG. 6 shows a partial cutaway view of various elements of exemplary flexible couplings and a guide housing, in accordance with aspects of the present invention.

FIG. 6 shows a partial cutaway view of various elements of exemplary flexible couplings and a guide housing, in accordance with aspects of the present invention. In FIG. 6, the flexible coupling elements shown include rigid connecting portions 401, 402 coupled by a joint 403, forming, for example, a universal-type joint. Angular or other motion of the portion 401 relative to the joint 403 may occur, for example, via bearings 404a, 404b (e.g., ball bearings), and similarly between joint 403 and portion 402. In addition, in the exemplary variation shown in FIG. 6, portion 401 includes extensions 401a, 401b receivable within slot recess 410a extending about the inner surface of generally cylindrically-shaped guide housing 410. The assembly of portions 401, 402, and 403 and related components may thereby rotate in direction $R_{45}$, with extensions 401a, 401b traveling within slot 410a.

In some variations, each of these elements 401, 402, 403, 404a, 404b may comprise a conductive material to enhance electrical communication therethrough. In addition, bearings 404a, 404b may be lubricated by an electrically conductive lubricant.

Figure 7:
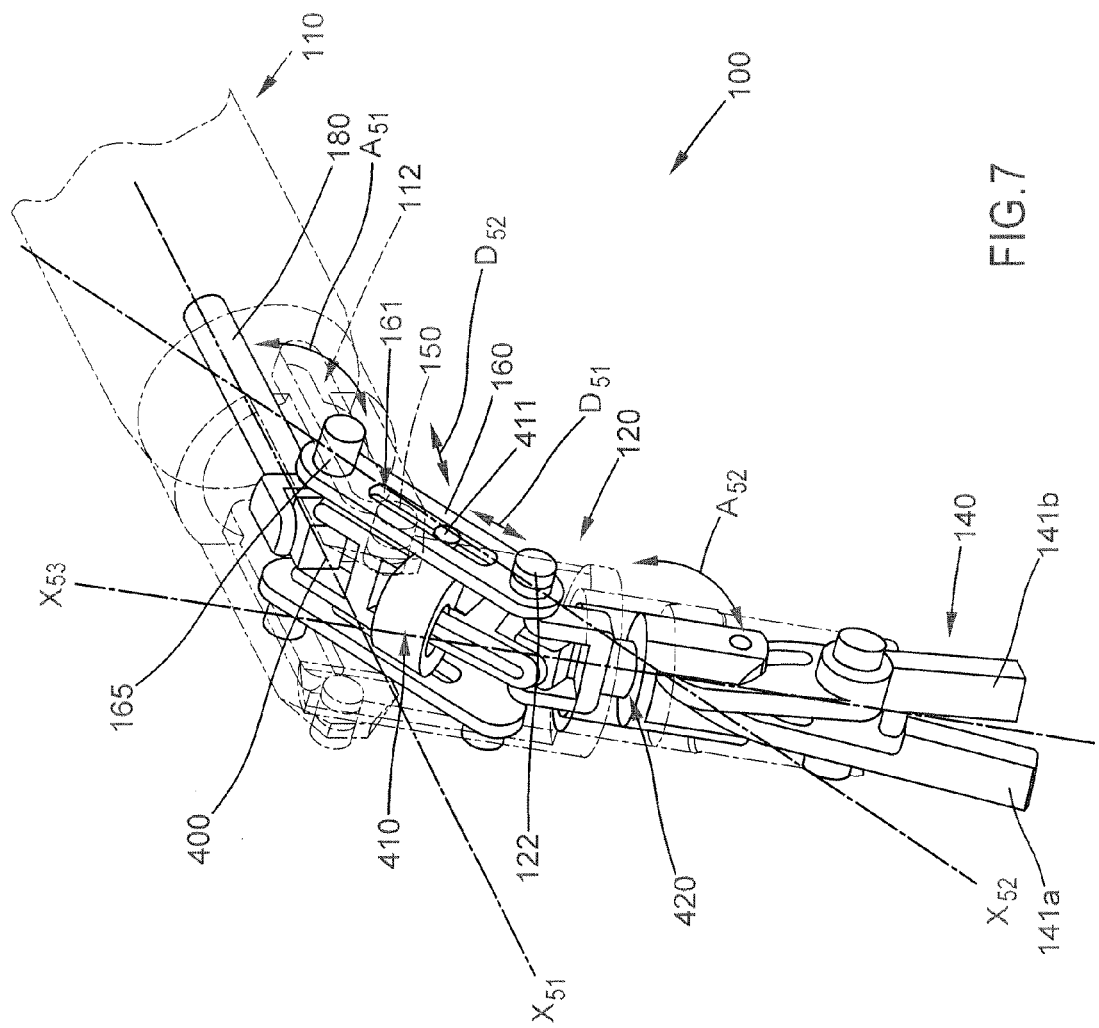
FIG. 7 presents a partial cutaway view of an exemplary flexible wrist-type element, in accordance with aspects of the present invention, in a similar position to that shown in FIG. 4.
Figure 17:
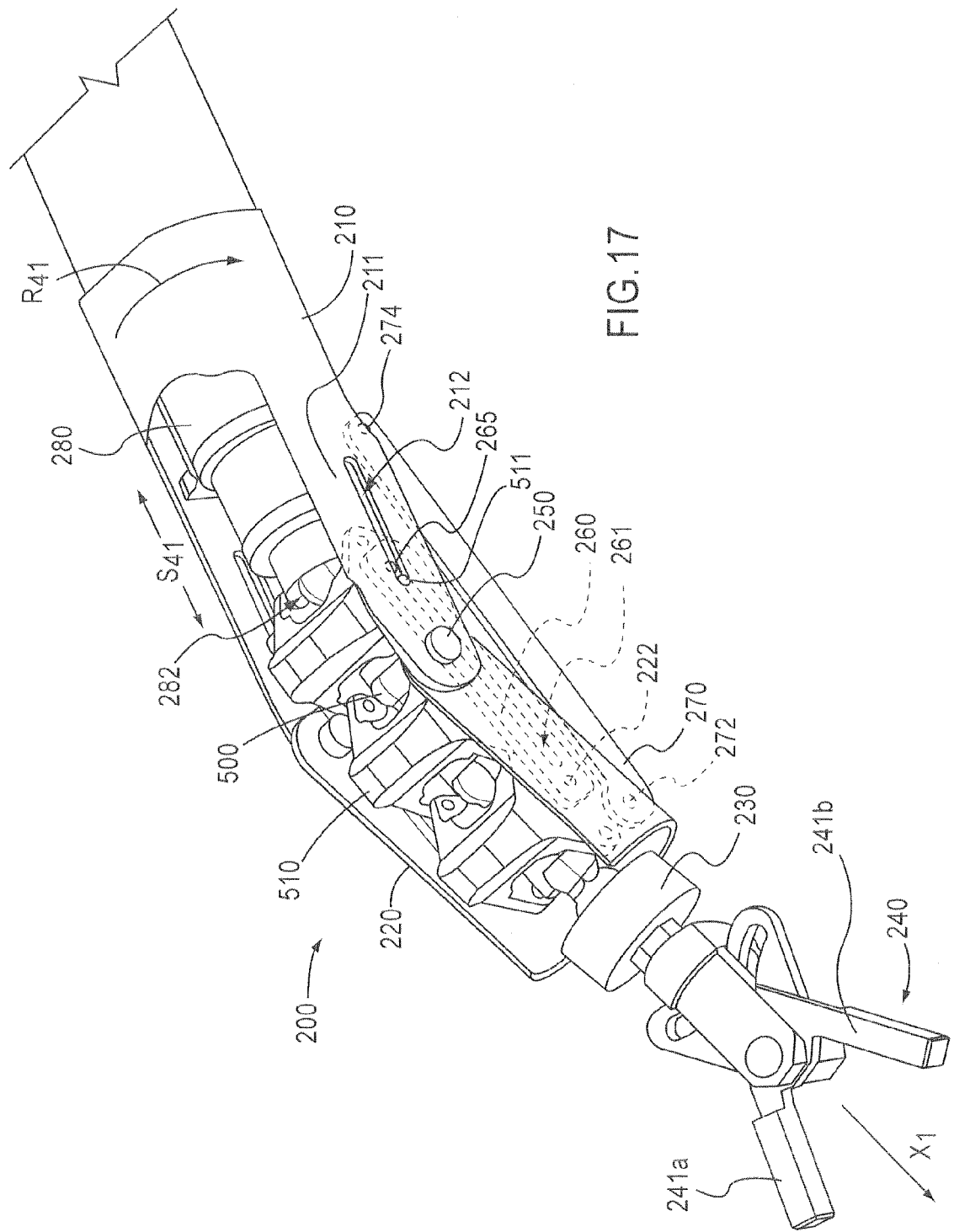
FIG. 17 shows a view of an exemplary flexible wrist-type element using an exemplary constant velocity joint, in accordance with an aspect of the present invention.

FIG. 7 presents a partial cutaway view of an exemplary flexible wrist-type element 100, in accordance with aspects of the present invention, oriented in a similar position to that shown in FIG. 4. As shown in FIG. 7, the guide 160 is angularly moved to an angle $A_{51}$ for its lengthwise axis $X_{52}$ relative to the axis $X_{51}$ of input mechanism 180, and end effector 420 is angularly moved to an angle $A_{52}$ for its lengthwise axis $X_{53}$ relative to the axis $X_{52}$ of the guide 160. Such angled movement of the guide 160 and end effector 420 relative to input mechanism 180 may be produced via operation of a control rod or other tendon-like mechanism, for example (not shown in FIG. 7). For example, the control rod or other tendon-like element may be a mechanism to transmit force, such as a link connected between the hub portion 120 and the body housing 110, as shown in FIG. 17 below. It is noted that extending pin 411, in the position shown in FIG. 7, is located at distance $D_{51}$ from a first end of slot 161, and pin 165 is located a distance $D_{52}$ from the first end of the slot 112. The movement of the pin 165 relative to the first end of the slot 112 results from the angled movement of the hub 120 and end effector 140 relative to the housing body 110.

Figure 8:
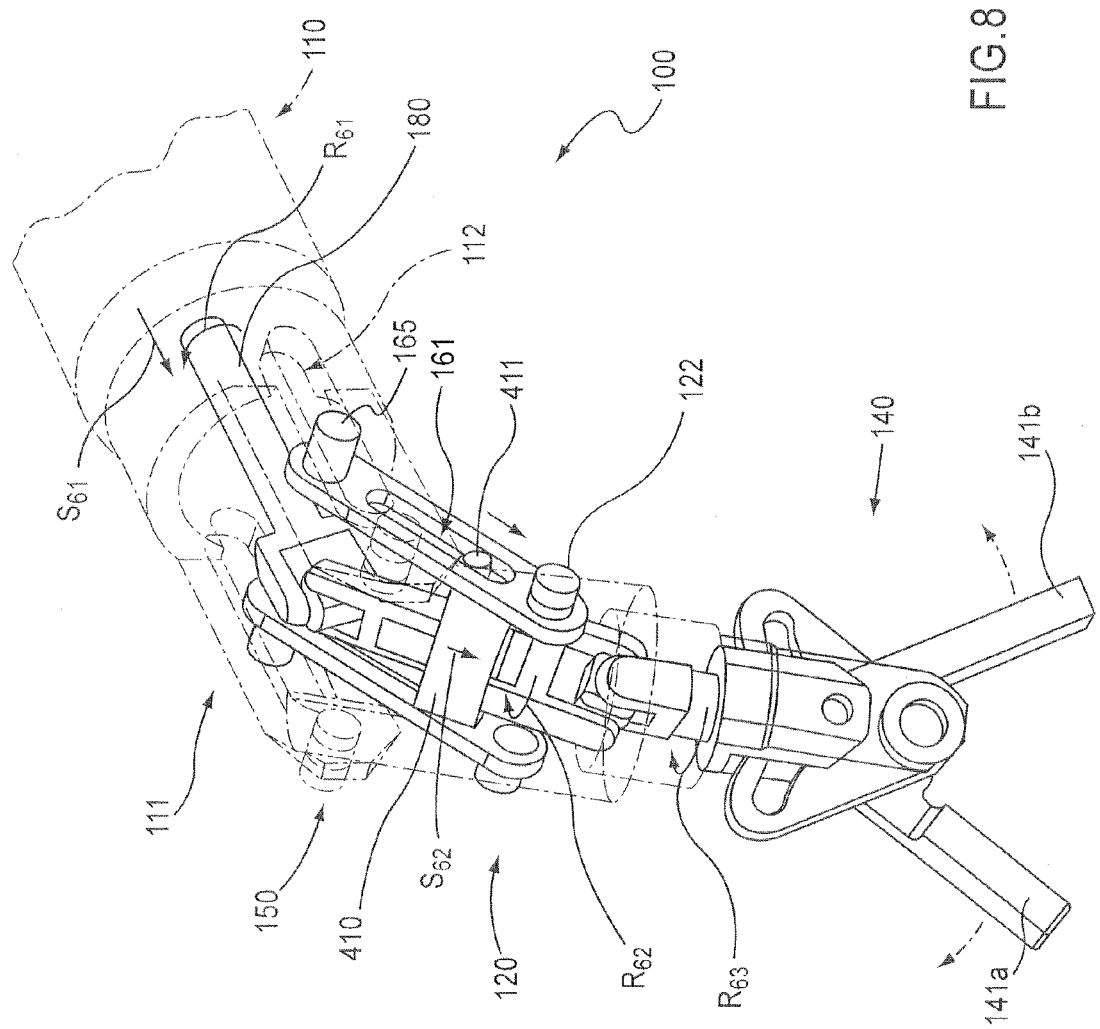
FIG. 8 contains a partial cutaway view of an exemplary flexible wrist-type element, in accordance with aspects of the present invention, having the angled position of the hub relative to the body portion in a similar orientation to that shown in FIG. 4, with the end effector in an open and first rotated position relative to that of FIG. 7.

FIG. 8 contains a partial cutaway view of an exemplary flexible wrist-type element 100, in accordance with aspects of the present invention, having an angularly moved position of the hub 120 relative to the input mechanism 180, in an orientation similar to that of FIG. 4, with the end effector 140 in an open and first rotated position relative to that shown in FIG. 7. In addition, input mechanism 180, in the position shown in FIG. 8, has slidably moved with flexible couplings 400 in the direction $S_{61}$, so as to extend the flexible coupling(s) 400 to a position such that extending pin 411 has moved to a location near the first end of slot 161. Guide housing 410, along with flexible coupling(s) 400, has correspondingly slid in direction $S_{62}$, relative to the position shown in FIG. 7.

As a result of the motion of the flexible coupling(s) 400 in the direction $S_{62}$ as indicated, extensions 141a, 141b have responsively moved from a first, more closed position as shown in FIG. 7 to a second, more open position, as shown in FIG. 8. Note that guide track pin 165 is freely slidable in slot 112 of extension 111, so that the overall drive train may slideably reach a least binding or otherwise suitable position via the pin 165 within slot 112.

Also as shown in FIG. 8, rotational motion may be communicated via the input mechanism 180 in the direction $R_{61}$, which is communicated to the end effector 140 in direction $R_{63}$ via flexible coupling(s) 400 in direction $R_{62}$.

Figure 9:
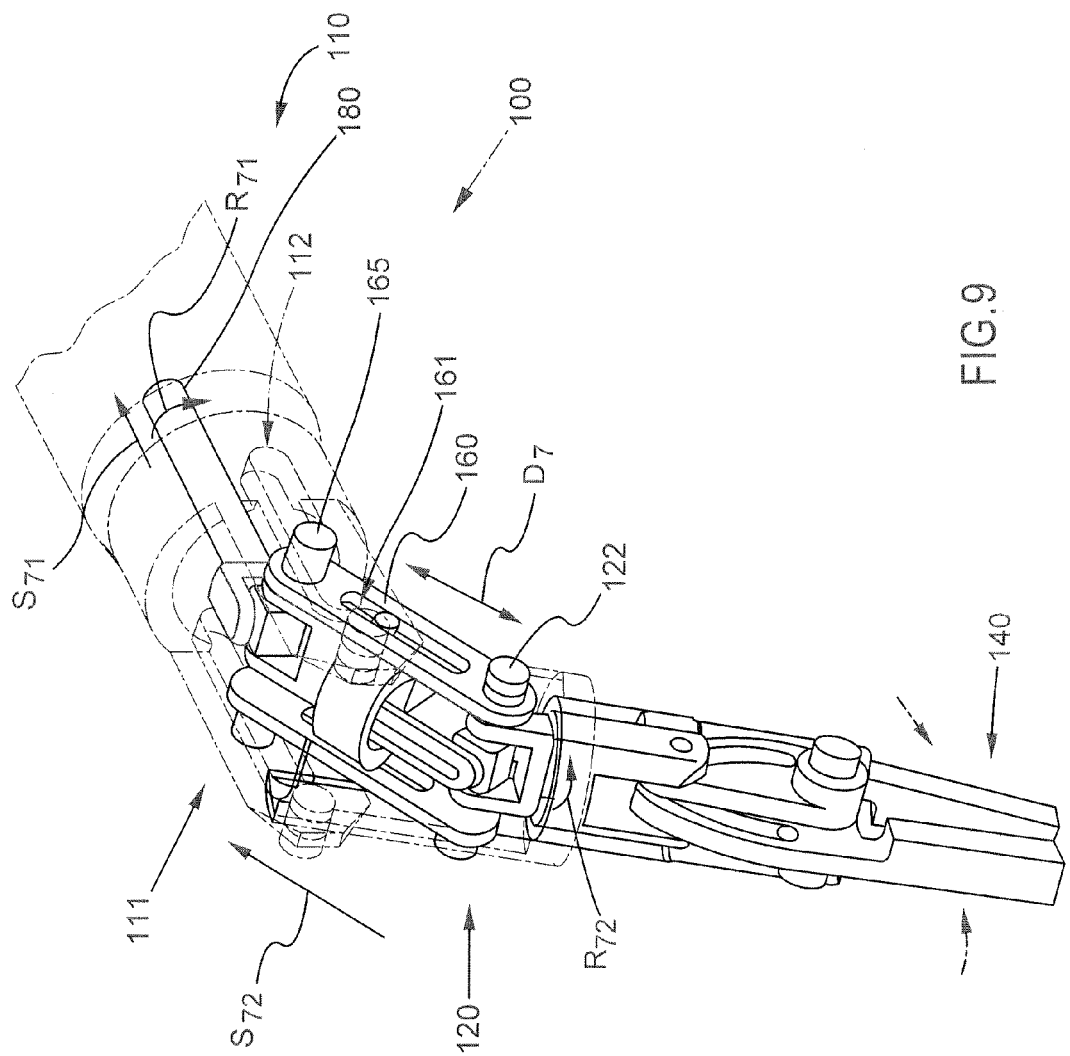
FIG. 9 shows a partial cutaway view of an exemplary flexible wrist-type element, in accordance with aspects of the present invention, having the angled position of the hub relative to the body portion in a similar position to that shown in FIG. 4, with the end effector in a closed position relative to that of FIG. 8.

FIG. 9 shows a partial cutaway view of the flexible wrist-type element 100 having the angularly moved position of the hub 120 relative to the body portion 110 as shown in FIG. 4, with the end effector 140 in a closed position relative to that shown in FIG. 8. In reverse of the motion shown in and described with respect to FIG. 8, FIG. 9 shows that motion of the input mechanism 180 in the direction $S_{71}$ moved flexible coupling(s) 400 in the direction $S_{72}$, as indicated. Thus, extensions 141a, 141b have moved from the second, more open position (FIG. 8) to the first, more closed position (FIG. 9). Note that guide track pin 165 is again freely slidable in slot 112 of extension 111, so that the overall drive train may slideably reach a least binding or otherwise suitable position.

Also similarly to as shown and described with respect to FIG. 8, the effect of rotational motion $R_{71}$ communicated via the input mechanism 180 to the end effector 140 in rotation direction $R_{72}$ is shown in FIG. 9.

Figure 10:
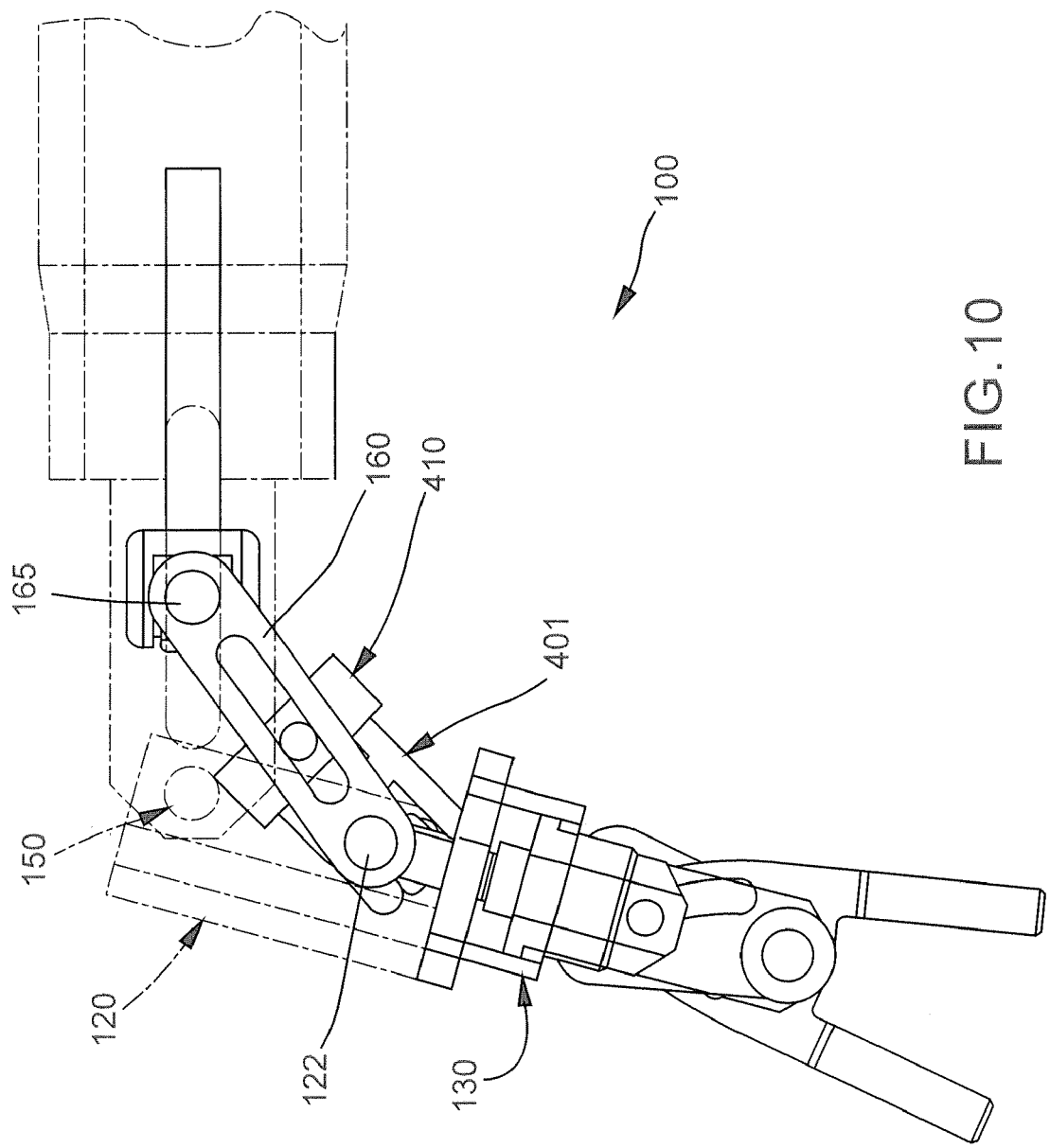
FIG. 10 shows a side, partial cutaway section view of an exemplary flexible wrist-type element, in accordance with aspects of the present invention, in a similar position to that shown in FIG. 4.

FIG. 10 shows a side, partial cutaway section view of the flexible wrist-type element 100 in a position similar to that shown in FIG. 4. The view of FIG. 10 is similar to that of FIG. 8, but more clearly shows the outer surface of the hub 120 and sleeve 130. In addition, a part of the rigid connecting portion 401 is visible in this view.

Figure 11:
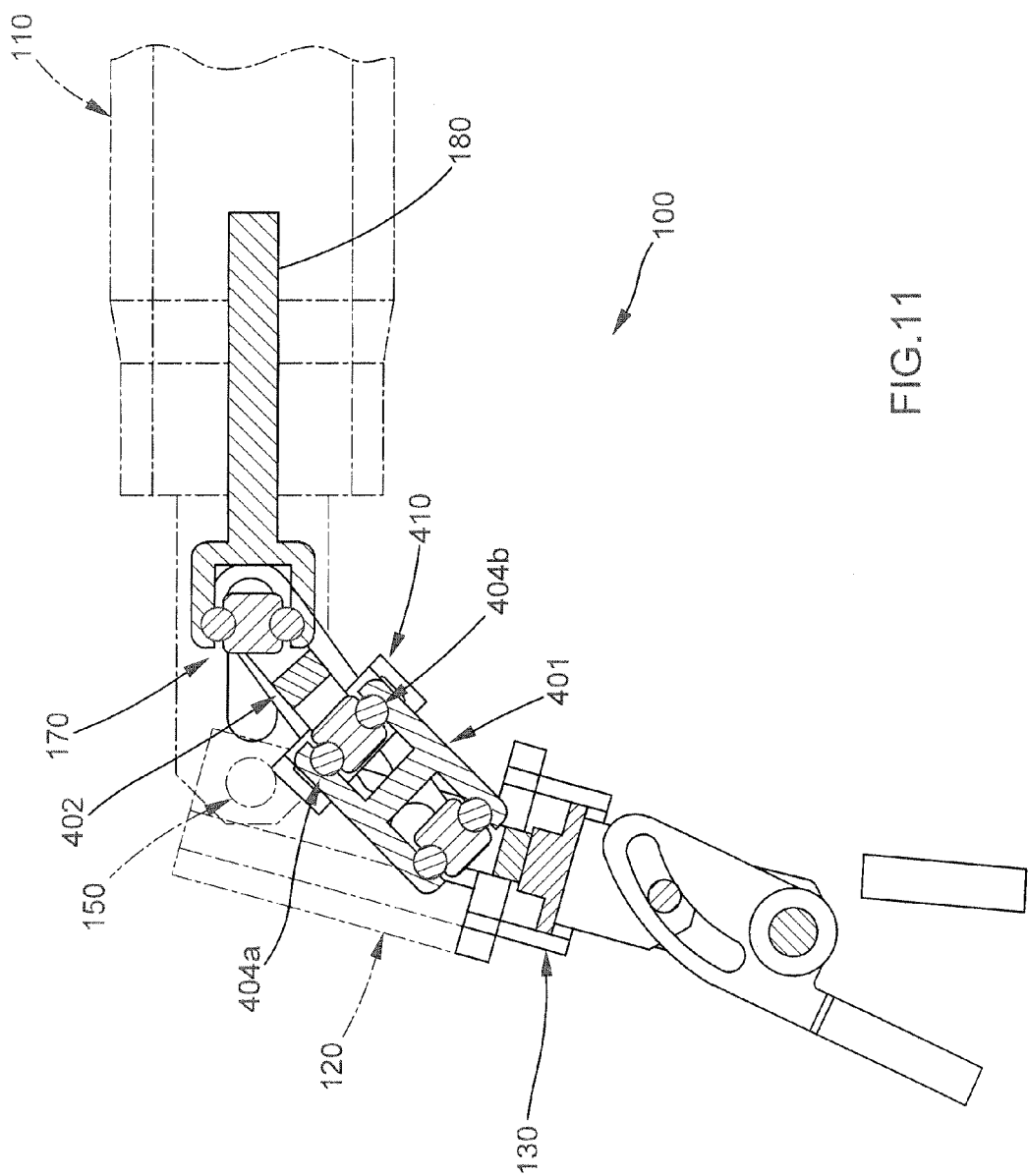
FIG. 11 presents a vertical cross-sectional view of an exemplary flexible wrist-type element, in accordance with aspects of the present invention, in a position similar to that shown in FIG. 10.
Figure 12:
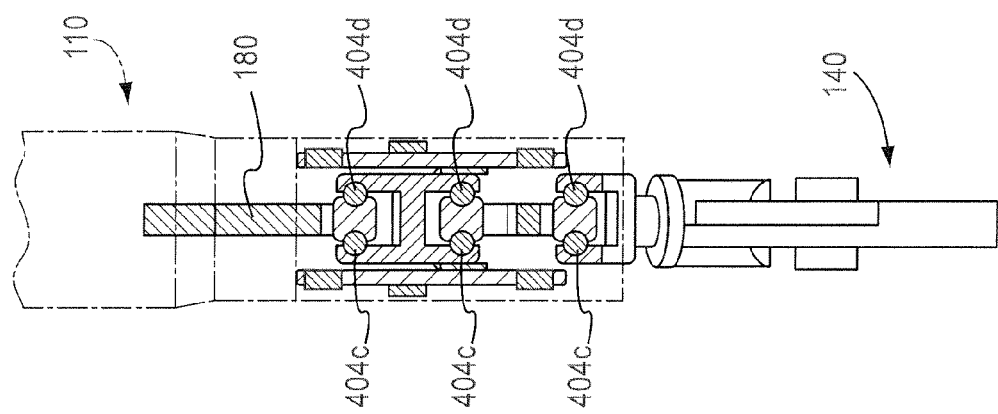
FIG. 12 presents a partial horizontal cross-sectional view of an exemplary flexible wrist-type element, in accordance with aspects of the present invention, in a position similar to that shown in FIG. 10.

FIGS. 11 and 12 present a representative vertical and axial cross-sectional view of the flexible wrist-type element 100 in a position similar to that shown in FIG. 10. Visible in the view of FIGS. 11 and 12 are the rigid connecting portions 401, 402 and bearings 404a, 404b spaced apart along a first axis and bearings 404a' and 404b' (not shown) spaced apart along a second axis, as well as other portions of flexible coupling elements, in accordance with aspects of the present invention. In this case, the second axis of bearings 404c and 404d is substantially perpendicular to the first axis of bearings 404a and 404b at each respective joint 403 (not shown). More specifically, additionally referring to FIG. 5, in this aspect, the rigid connecting portions 401 and 402 include a shaft portion and an extension portion, such as a C-arm type or fork-like structure. As such, each arm of the C-arm structure is movably connected to one pair of the spaced bearings on a given axis, such that adjacent C-arms lie in substantially perpendicular planes, thereby allowing each joint 403 to fix adjacent rigid structures to rotate together but to allow relative angular changes. Also, one or joints 170 of the plurality of couplings in this aspect include a universal joint having a central block supporting horizontal and vertical pairs of ball bearings that movably connect to fork-like connector elements of the flexible coupling. As such, joints 170 allow for variable angular movement between coupling elements, and the joints 170 also transfer axial and torsional forces. Other U-joint designs could be used.

Figure 13:
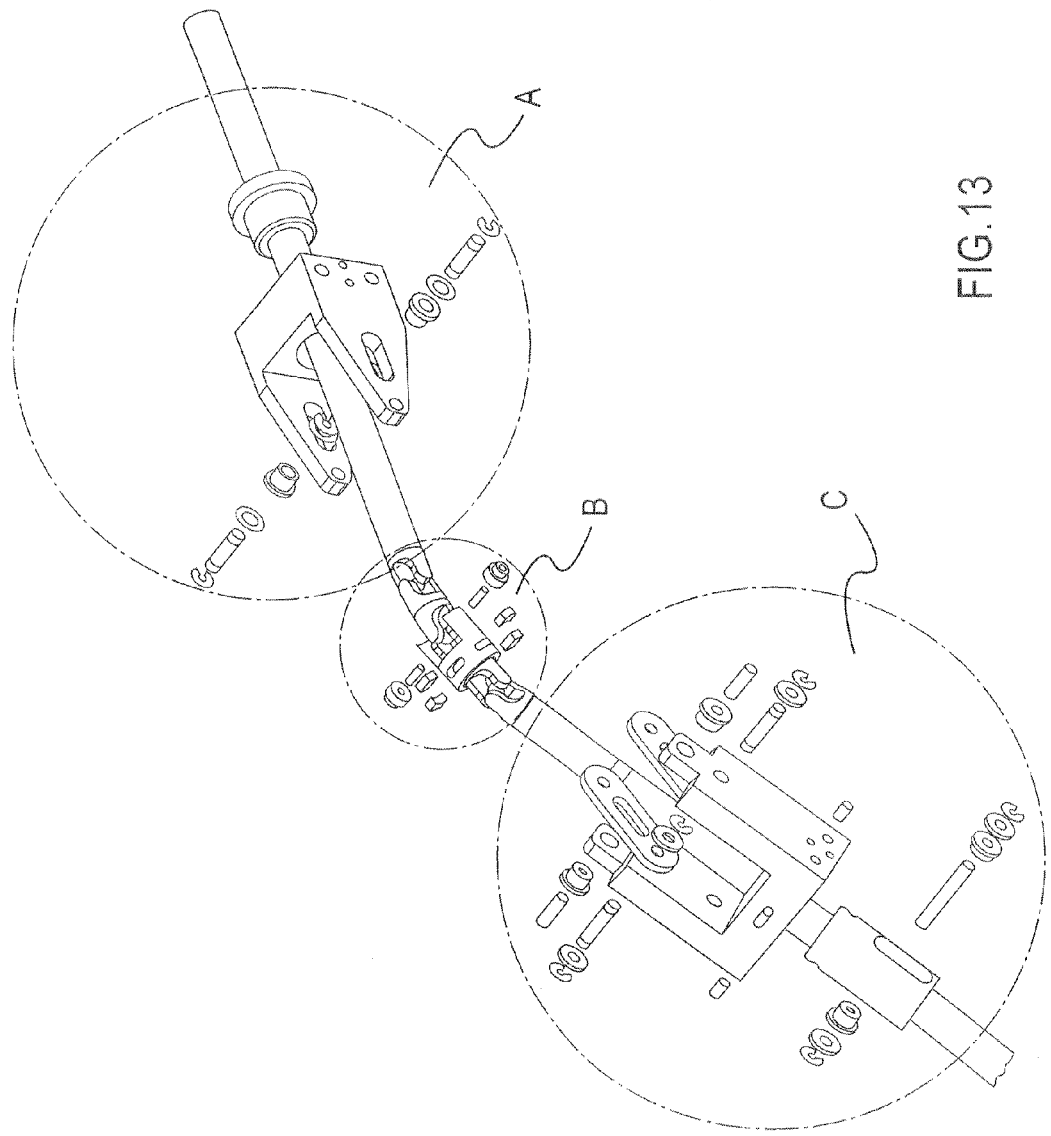
FIG. 13 presents an exploded and disassembled view of various components of a portion of an exemplary drive train, in accordance with another variation of the present invention.

FIG. 13 presents an exploded and disassembled view of various components of a portion of an exemplary drive train, in accordance with another variation of the present invention. Element A of FIG. 13 is an exemplary housing extension, which is further detailed in FIG. 14. Element B of FIG. 13 is an exemplary flexible coupling element and guide housing, which are further detailed in FIG. 15. Element C of FIG. 13 shows an exemplary hub and guide, and other portions relating thereto, as further detailed in FIG. 16.

Figure 14:
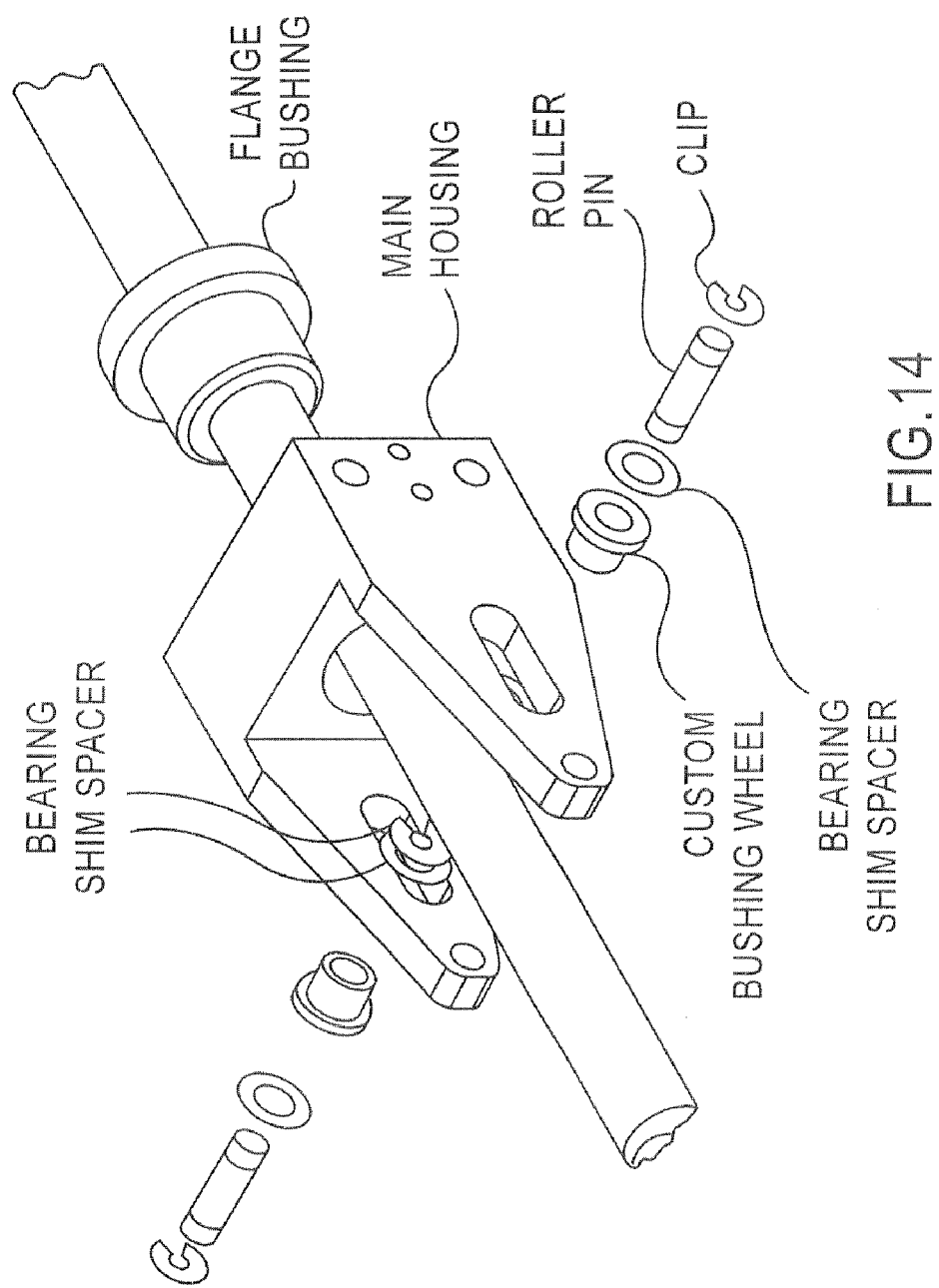
FIG. 14 shows another variation of an exemplary housing extension, in accordance with aspects of the present invention.

Referring now to FIG. 14, illustrated is an exemplary housing extension in accordance with an aspect of the present invention. The housing extension includes a "U" shaped main housing surrounding a shaft, e.g., a control rod, which extends through the center of the main housing. The shaft is coupled to the main housing via a flange bushing. The main housing also includes a pair of movement limiting travel mechanisms, such as a slot, which limits travel of a pair of slidable roller pins. The slidable roller pins are coupled to the slot via a custom bushing wheel. The slidable roller pins are inserted into the custom bushing wheel. The slidable roller pins are held within the custom bushing wheel via bearing shim spacers and a C-clip. The slidable roller pins move within a slot of an outer link (not shown). The movement of the slidable roller pin in the outer link limits the angular movement of the main housing.

Figure 15:
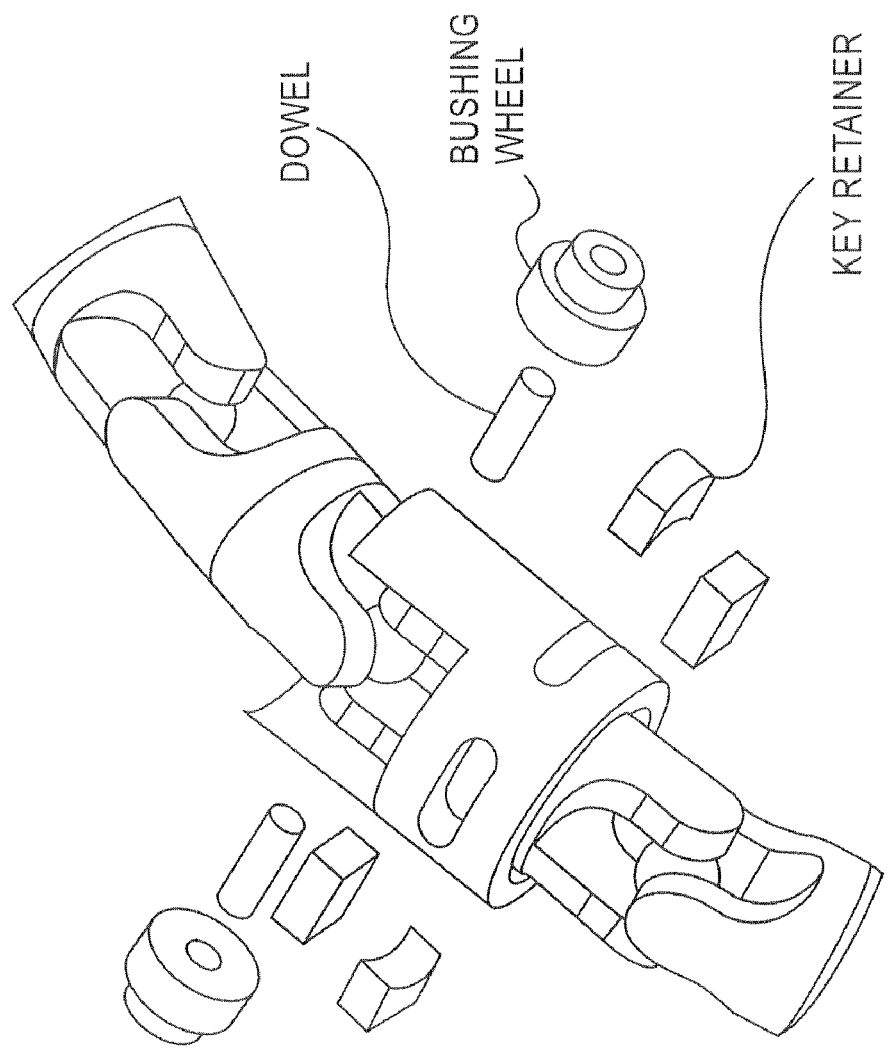
FIG. 15 shows another variation of an exemplary flexible coupling element and guide housing, in accordance with aspects of the present invention.

Turning now to FIG. 15, illustrated is an exemplary flexible coupling element and guide housing in accordance with an aspect of the present invention. The guide housing surrounding the chain of flexible couplings includes a pair of dowels coupled to opposite sides of the guide housing extending into a pair of bushing wheels. The pair of bushing wheels travel within a slot of a guide track (not shown) limiting the movement of the chain of flexible couplings. A key retainer is coupled to the guide housing surrounding the chain of flexible couplings limiting the rotational movement of the flexible couplings.

Figure 16:
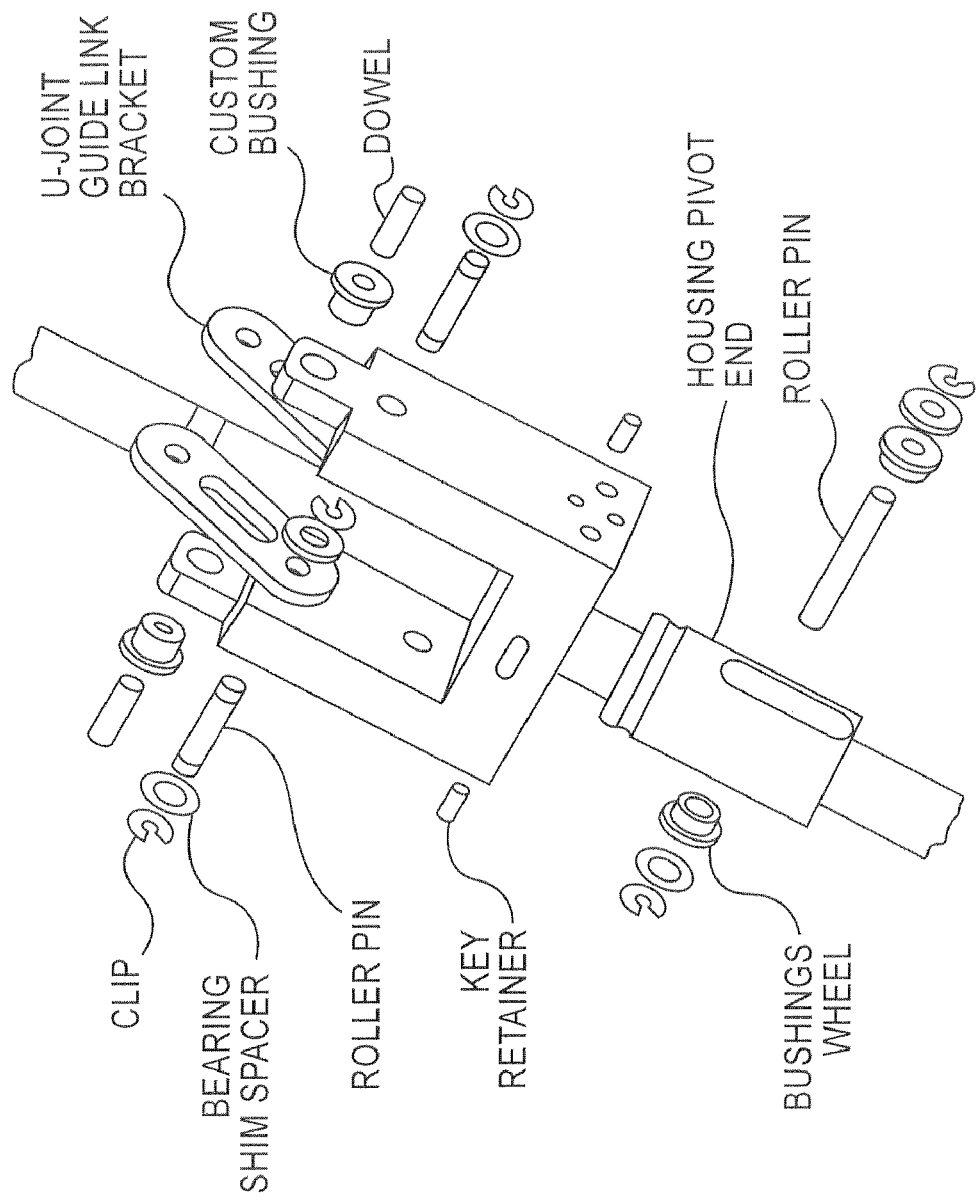
FIG. 16 shows another variation of an exemplary hub and guide, in accordance with aspects of the present invention.

Referring now to FIG. 16, illustrated is another variation of an exemplary "U" shape hub and guide in accordance with aspects of the present invention. The hub surrounds a shaft extending through the middle of the hub. A pair of U-joint guide link brackets are coupled to the inside of the hub via a dowel extending through a pair of custom bushings. Each dowel is held within the custom bushings by bearing shim spacers and a C-clip. The U-joint guide link brackets are connected to an outer link (not shown) limiting the movement of the hub by the dowels sliding in a slot of the outer link. The hub includes a housing pivot end coupled to the outer link via a roller pin extending through the housing pivot end. The roller pin is inserted into bushing wheels and held in place with bearing shim spacers and a C-clip. The roller pin slides in the slot of the outer link limiting the movement of the housing pivot end.

One variation of the present invention may involve using different types or structures for the flexible couplings (e.g., different Hooke's joints or universal joints). FIG. 17 illustrates a view of an exemplary flexible wrist-type element 200 using a constant velocity Hooke's joint, in accordance with an aspect of the present invention. As shown in FIG. 17, the flexible wrist-type element 200 has a body housing 210 that is coupled to or otherwise operably engages a hub 220. Among other things, the hub may move angularly relative to the housing 210 about, for example, one or more pivot points 250. Such angular operation may occur via a control rod or other tendon-like element, for example, a link 270, which may be driven by a drive system similar to drive system 191, as discussed above. The link 270 may be secured at one end to the body housing 210 via a first pin 274 and secured to the hub 220 via a second pin 272. An end effector or other tool or component 240 (also interchangeably and/or collectively referred to herein as an "end effector") is engaged with the hub 220, such as via a sleeve 230 that allows relative rotation with respect to the hub 220.

Extending from the interior of housing body 210 is an input mechanism (e.g., shaft) 280. Coupled to or otherwise operable to the input mechanism 280 are one or more constant velocity joints 500, as well as one or more guide housings 510 for securing and/or limiting the travel of one or more of the constant velocity joints 500. Each constant velocity joint 500 has a guide housing 510 or is otherwise attached to a travel limiting movement mechanism. In the variation shown, the guide housing 510 coupled to the middle constant velocity joint 500 has a support element or pin 511 slidable within a guide 260 for limiting the movement of the constant velocity joints 500. In the exemplary variation shown in FIG. 17, three constant velocity joints 500 are coupled in series to the input mechanism 280, and the guide 260 is secured at one end via a first pin 265 slidable within slot 212 and at a second end via a second pin 222 secured to the hub 220.

Figure 18:
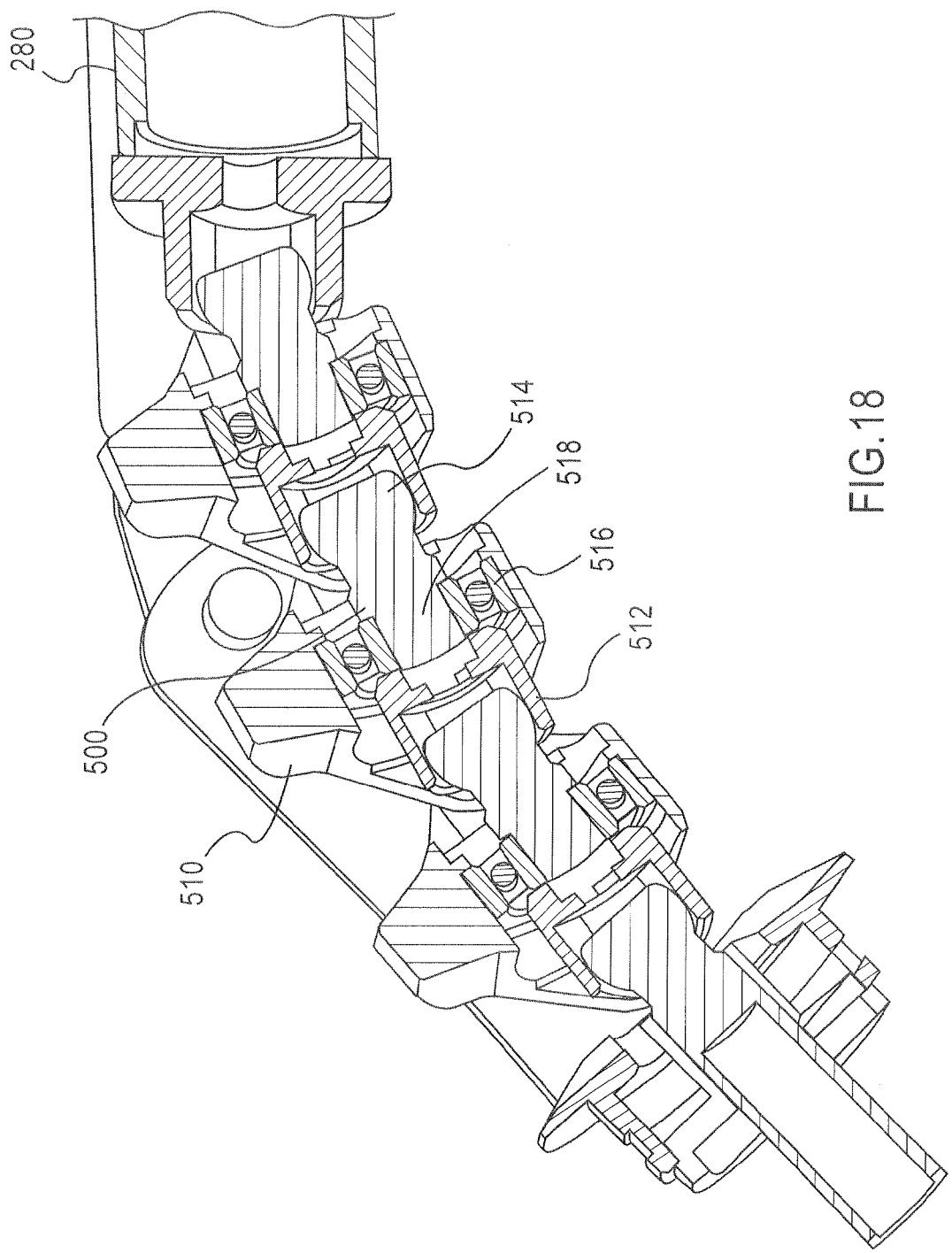
FIG. 18 presents a partial cutaway view of one exemplary flexible wrist-type element, in accordance with aspects of the present invention, in a similar position to that shown in FIG. 17.

FIG. 18 illustrates a partial cutaway view of an exemplary flexible wrist-type element 200 in a similar position to that shown in FIG. 17. As shown in FIG. 18, extending from the interior of housing body 210 is an input mechanism (e.g., shaft) 280. Three constant velocity joints 500 are coupled in series to the input mechanism 280.

Each constant velocity joint 500 may have a first portion 514, such as a male end, and a second portion 512, such as a female end, and a shaft 518 connecting the portions 514 and 516. Further, each portion 514 and 516 has cooperating structure to allow the transfer of rotational forces and/or axial forces upon oblique positioning of the portions. In the illustrated aspect, for example, the female portion 512 may have an inner wall defining an opening sized to fit a corresponding male portion 514. In an aspect, for example, the male portions 514 may have a rounded hexagonal shape and the female portions 512 may have a corresponding hexagonal shape opening. The male portions 514 may be coupled to the female portions 512, e.g., in a ball and socket arrangement, in alternating assemblies, as illustrated in FIG. 18. The rounded hexagonal shape of the male portion allows the constant velocity joints to rotate in any direction. Additionally, the hexagonal shape of the male portion provides a transfer of torque to the shaft of the constant velocity joints. Additionally, it should be noted that a bearing may be positioned between the cooperating structures of the portions 514 and 516. Further, each constant velocity joint 500 may also include a bearing 516 between the shaft 518 and the guide housing 510. As such, the guide housings 510 may be coupled to the bearings 516 to allow relative rotation between the shaft 518 and the guide housing 510.

Referring back to FIG. 17, in exemplary operation, for example, input mechanism 280 comprises an input shaft coupled to the constant velocity joints 500, which in this aspect includes three constant velocity joints coupled in series, the constant velocity joints 500 being further coupled to the end effector 240 via an end effector shaft (one or more of the input mechanism 280, the constant velocity joints 500, and/or parts of the end effector 240 interchangeably also being referred to herein as a "drive train"). The guide 260 is secured and/or limited in movement at its two ends by a first pin 265 that travels within the slot 212 of extension 211 and by a second pin 222 attached to the hub 220. The guide housing 510 coupled to the middle of the three constant velocity joints in series includes an extending pin 511 that is limited in its travel by slot 261 of guide 260. It is noted that, in the position shown in FIG. 15, the first pin 265 is located near a first end of the slot 212.

The input shaft of the input mechanism 280 may be moved (e.g., by sliding) toward and away from the constant velocity joints 500 (e.g., in direction $S_{41}$ as shown in FIG. 17). As discussed above, a drive system 191 (e.g., hydraulic, mechanical, magnetic and/or electrical) may be coupled to the input mechanism 280 causing the movement of the input mechanism 280. This motion in turn produces motion (e.g., in direction $S_{41}$ in the orientation of the device 200 shown in FIG. 17) of the constant velocity joints, which may travel together with the guide housing 510 within the limits of slot 261. Among other things, the guide housing 510 ensures that the three constant velocity joints do not pivot significantly relative to one another in a direction other than the direction of travel (i.e., generally in direction $S_{41}$ as shown in FIG. 17). The motion in direction $S_{41}$ of the universal joints may in turn affect the end effector 240, such as by causing the extensions 241a, 241b to open and close.

The input shaft 280 as shown in FIG. 17 may also be rotated, for example, in directions $R_{41}$, which in one aspect correspondingly rotates the constant velocity joints and the end effector in the same direction, however, the connections may also be setup such that rotation of input shaft 280 in one direction causes the joints and/or the end effector to rotate in an opposite direction. Further, in general for this aspect or for the earlier discussed aspects, it should be noted that a rotational input may be transferred to either a rotational or axial output, and an axial input may be transferred to either an axial or rotational output, depending on a configuration of the connecting structures.

Another variation of aspects of the present invention includes using two flexible coupling members in a chain connected to an input mechanism and an end effector. This aspect may not require a guide housing surrounding the flexible coupling members.

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

What is claimed is:

1. A flexible wrist-type element, comprising: a body housing extending along a first longitudinal axis;
a hub at least partially extending along a second longitudinal axis and movably connected to the body housing, wherein the hub comprises a first end movable to a first position defining a first angle between the second longitudinal axis and the first longitudinal axis of the body housing, wherein the first angle is variable;
a plurality of couplings comprising a plurality of elements movably interconnected by a plurality of joints, wherein the plurality of couplings are movably positionable relative to the body housing and the hub, wherein the plurality of couplings have an input end adjacent to the body housing and an opposing output end adjacent to the first end of the hub, wherein the input end is configured to receive an input force comprising at least one of an axial force or a torsional force, and wherein the plurality of couplings are configured to transmit at least a portion of the input force from the input end to the output end when the first end of the hub is in the first position defining the first angle;

wherein the body housing comprises an extension adjacent to the hub, wherein the extension comprises an inner wall defining a surface, wherein at least one of the plurality of couplings are in movable contact with the surface, wherein the surface defines limits for movement of the plurality of couplings relative to the body housing and the hub; and wherein the extension extends along a third longitudinal axis, and wherein the surface defines a slot having a first length substantially parallel to the third longitudinal axis and a second length substantially perpendicular to the third longitudinal axis, wherein the first length is greater than the second length.

2. The flexible wrist-type element of claim 1, further comprising a guide element movably connected to the body housing and the hub, wherein the guide element is further movably connected to the plurality of couplings and further comprises a surface, where the surface defines limits for movement of the plurality of couplings.

3. The flexible wrist-type element of claim 2, wherein the guide element is movable to a second angle relative to the body housing when the first end of the hub is in the first position defining the first angle relative to the body housing, wherein the second angle is less than the first angle.

4. The flexible wrist-type element of claim 3, wherein the guide element comprises opposing ends, wherein the first guide end is rotatably connected to a first one of the body housing or the hub adjacent to a first one of the opposing ends, and wherein the guide element is slidably connected to a second one of the body housing or the hub adjacent to a second one of the opposing ends.

5. The flexible wrist-type element of claim 1, further comprising a guide housing movably connected to the body housing and the hub, wherein the guide housing is further movably connected to at least one of the plurality of couplings and comprises a support surface supporting the at least one of the plurality of couplings during movement of the first end of the hub to the first position defining the first angle.

6. The flexible wrist-type element of claim 5, wherein the support surface limits an amount of pivoting between the plurality of couplings.

7. The flexible wrist-type element of claim 5, wherein the support surface prevents portions of the plurality of couplings from collapsing under compression and maintains alignment of the plurality of couplings under extension.

8. The flexible wrist-type element of claim 5, wherein the body housing comprises an extension adjacent to the hub, wherein the extension comprises an inner wall defining a first slot, wherein the guide housing further comprises a support element, and further comprising a guide element having a first guide end, a second guide end and a second slot, wherein the first guide end is movably connected to the body housing within the first slot, wherein the second guide end is movably connected to the hub, and wherein the support element of the guide housing is movably connected within the second slot of the guide element such that the second slot defines a limit for movement of the plurality of couplings.

9. The flexible wrist-type element of claim 8, wherein the first slot defines an angular limit of the first angle, and wherein the second slot defines an axial limit of movement of the plurality of couplings in response to the input force comprising the axial force.

10. The flexible wrist-type element of claim 5, wherein the guide housing is connected to the at least one of the plurality of couplings at one of the plurality of joints.

11. The flexible wrist-type element of claim 5, further comprising a bearing element positioned between the support surface and the at least one of the plurality of couplings, wherein the bearing element allows the at least one of the plurality of couplings to rotate relative to the guide housing.

12. The flexible wrist-type element of claim 1, wherein each of the plurality of joints comprises a universal joint or a Hooke's joint.

13. The flexible wrist-type element of claim 1, wherein each of the plurality of joints comprises a first pair of ball bearings, spaced apart along a first axis, supporting a first one of the plurality of elements and a second pair of ball bearings, spaced apart along a second axis, supporting a second one of the plurality of elements, wherein the first axis is substantially perpendicular to the second axis.

14. The flexible wrist-type element of claim 1, wherein each of the plurality of joints comprises a constant-velocity joint.

15. The flexible wrist-type element of claim 1, wherein each of the plurality of elements comprises a first rigid end having a first engagement surface and a second rigid end having a second engagement surface, wherein each of the plurality of joints is defined by a movable interaction between the first engagement surface of a respective first element and the second engagement surface of a respective second element, wherein one of the first engagement surface and the second engagement surface comprises a curved surface.

16. The flexible wrist-type element of claim 15, wherein each of the plurality of elements further comprises a shaft portion connecting the first rigid end and the second rigid end, further comprising a guide housing having an extending support element and a connection with the shaft that allows relative rotation and prevents relative axial movement, and further comprising a guide element movably connected to the body housing and the hub, wherein the guide element comprises a surface movably connected to the support element of the guide housing, wherein the surface defines limits for movement of the plurality of couplings.

17. The flexible wrist-type element of claim 1, wherein the plurality of joints comprise at least three joints.

18. The flexible wrist-type element of claim 1, further comprising a drive system having an input mechanism coupled to the input end of the plurality of couplings, wherein the drive system generates the input force.

19. The flexible wrist-type element of claim 18, wherein the drive system further generates another force to move the first end of the hub to the first position defining the first angle.

20. The flexible wrist-type element of claim 18, wherein the drive system further comprises at least one of an electric system, a hydraulic system, a magnetic system, or a mechanical system.

21. The flexible wrist-type element of claim 1, further comprising a drive system having an input mechanism coupled to the input end of the plurality of couplings, wherein the drive system comprises a manually-driven hydraulic system.

22. The flexible wrist-type element of claim 1, further comprising an end effector coupled to the output end of the plurality of couplings, wherein the end effector moves in response to receiving at least the portion of the input force transmitted by the plurality of couplings.

23. The flexible wrist-type element of claim 22, wherein the end effector comprises a surgical tool.

24. The flexible wrist-type element of claim 1, further comprising:
a manually-driven hydraulic drive system having an input mechanism coupled to the input end of the plurality of couplings, wherein the drive system generates the input force; and
an end effector coupled to the output end of the plurality of couplings, wherein the end effector comprises a surgical tool and moves in response to receiving at least the portion of the input force transmitted by the plurality of couplings.

25. The flexible wrist-type element of claim 1, wherein at least one of the body housing and the hub comprise an electrically non-conductive material, and further comprising an end effector connected to the hub and in communication with an electrically conductive portion within the body housing and the hub, wherein the end effector is configured to receive an electrical current delivered via the electrically conductive portion.

26. A flexible wrist-type element, comprising:
a body housing extending along a first longitudinal axis;
a hub at least partially extending along a second longitudinal axis and movably connected to the body housing, wherein the hub comprises a first end movable to a first position defining a first angle between the second longitudinal axis and the first longitudinal axis of the body housing, wherein the first angle is greater than zero degrees;
a plurality of couplings comprising a plurality of elements movably interconnected by a plurality of joints, wherein the plurality of couplings are movably positionable relative to the body housing and the hub, wherein the plurality of couplings have an input end adjacent to the body housing and an opposing output end adjacent to the first end of the hub, wherein the input end is configured to receive an input force comprising at least one of an axial force or a torsional force, and wherein the plurality of couplings are configured to transmit at least a portion of the input force from the input end to the output end when the first end of the hub is in the first position defining the first angle;
a guide element movably connected to the body housing, the hub and the plurality of couplings, wherein the guide element further comprises a surface that defines limits for movement of the plurality of couplings, wherein the guide element is movable to a second angle relative to the body housing when the first end of the hub is in the first position defining the first angle relative to the body housing, wherein the second angle is less than the first angle; and
a guide housing connected to the body housing and the hub via a movable connection with the guide element, wherein the guide housing is further movably connected to at least one of the plurality of couplings and comprises a support surface supporting the at least one of the plurality of couplings during movement of the first end of the hub to the first position defining the first angle.

27. The flexible wrist-type element of claim 26, further comprising:
a manually-driven hydraulic drive system having an input mechanism coupled to the input end of the plurality of couplings, wherein the drive system generates the input force; and
an end effector coupled to the output end of the plurality of couplings, wherein the end effector comprises a surgical tool and moves in response to receiving at least the portion of the input force transmitted by the plurality of couplings.

28. A flexible wrist-type element, comprising:
a body housing extending along a first longitudinal axis;
a hub at least partially extending along a second longitudinal axis and movably connected to the body housing, wherein the hub comprises a first end movable to a first position defining a first angle between the second longitudinal axis and the first longitudinal axis of the body housing, wherein the first angle is greater than zero degrees;
a plurality of couplings comprising a plurality of elements movably interconnected by a plurality of joints, wherein the plurality of couplings are movably positionable relative to the body housing and the hub, wherein the plurality of couplings have an input end adjacent to the body housing and an opposing output end adjacent to the first end of the hub, wherein the input end is configured to receive an input force comprising at least one of an axial force or a torsional force, and wherein the plurality of couplings are configured to transmit at least a portion of the input force from the input end to the output end when the first end of the hub is in the first position defining the first angle;
a guide element movably connected to the body housing, the hub and the plurality of couplings, wherein the guide element further comprises a surface that defines limits for movement of the plurality of couplings, wherein the guide element is movable to a second angle relative to the body housing when the first end of the hub is in the first position defining the first angle relative to the body housing, wherein the second angle is less than the first angle;
a guide housing connected to the body housing and the hub via a movable connection with the guide element, wherein the guide housing is further movably connected to at least one of the plurality of couplings and comprises a support surface supporting the at least one of the plurality of couplings during movement of the first end of the hub to the first position defining the first angle;
a drive system having an input mechanism coupled to the input end of the plurality of couplings, wherein the drive system generates the input force; and
an end effector coupled to the output end of the plurality of couplings, wherein the end effector moves in response to receiving at least the portion of the input force transmitted by the plurality of couplings.

29. The flexible wrist-type element of claim 28, wherein the drive system comprises a manually-driven hydraulic system, and wherein the end effector comprises a surgical tool.

* * * * *